(12) United States Patent
Lüdemann et al.

(10) Patent No.: US 8,420,406 B2
(45) Date of Patent: Apr. 16, 2013

(54) METHOD FOR ANALYSING METABOLITES

(75) Inventors: Alexander Lüdemann, Potsdam (DE);
Alexander Erban, Berlin (DE);
Cornelia Wagner, Penzberg (DE);
Joachim Kopka, Berlin (DE)

(73) Assignee: Max-Planck-Gessellschaft zur Forderung der Wissenschaften E.V., Berlin (DE)

( * ) Notice: Subject to any disclaimer, the term of this patent is extended or adjusted under 35 U.S.C. 154(b) by 652 days.

(21) Appl. No.: 10/580,024

(22) PCT Filed: Dec. 17, 2004

(86) PCT No.: PCT/EP2004/014450
§ 371 (c)(1),
(2), (4) Date: Sep. 5, 2006

(87) PCT Pub. No.: WO2005/059556
PCT Pub. Date: Jun. 30, 2005

(65) Prior Publication Data
US 2007/0141712 A1    Jun. 21, 2007

(51) Int. Cl.
*G01N 37/00*    (2006.01)
(52) U.S. Cl.
USPC ............... 436/173; 436/56; 436/63; 436/95; 436/179; 435/4; 435/14; 435/29; 250/282; 250/299
(58) Field of Classification Search ............ 436/56, 436/57
See application file for complete search history.

(56) References Cited

U.S. PATENT DOCUMENTS

| | | | | |
|---|---|---|---|---|
| 5,532,206 A | * | 7/1996 | Evans et al. | 504/176 |
| 6,872,516 B2 | * | 3/2005 | Evans et al. | 435/3 |
| 2003/0077572 A1 | * | 4/2003 | Abramson et al. | 435/4 |
| 2003/0180710 A1 | * | 9/2003 | Lee et al. | 435/4 |
| 2004/0081994 A1 | * | 4/2004 | Hellerstein | 435/6 |
| 2005/0112706 A1 | * | 5/2005 | Kasper | 435/7.23 |

FOREIGN PATENT DOCUMENTS

| | | |
|---|---|---|
| CA | 2547755 | 6/2005 |
| EP | 1686372 A1 | 8/2006 |
| WO | WO 00/67017 | 11/2000 |

OTHER PUBLICATIONS

C. Birkemeyer et al., J. Chromatography A 993:89, 2003.*
M.K. Hellerstein and R.A. Neese, Am J Physiol Endocrinol Metab 276: 1146-1170, 1999.*

(Continued)

*Primary Examiner* — In Suk Bullock
*Assistant Examiner* — Timothy G Kingan
(74) *Attorney, Agent, or Firm* — Foley & Lardner LLP

(57) ABSTRACT

Described is a method for analyzing the metabolites of a biological sample which comprises quantitatively determining one or more metabolites in said sample in a way that said quantitative determination resolves isotopic mass differences within one metabolite, said method being characterized in that the sample comprises or is derived from a cell which has been maintained under conditions allowing the uptake of an isotopically labeled metabolizable compound so that the metabolites in said cell are saturated with the isotope with which said metabolizable compound is labeled. This method may further comprise, prior to quantitative determining the metabolites, combining the biological sample (i.e. the first biological sample) with a second biological sample in which the metabolites are not isotopically labeled or are isotopically labeled differently from the first biological sample; and determining in said biological samples the relative quantity of metabolites which differ by their isotopical label. Furthermore described is a set of isotopically labeled metabolites obtainable by applying this method, as well as kits facilitating the application of this method and corresponding uses.

14 Claims, 21 Drawing Sheets

OTHER PUBLICATIONS

Figure 1:
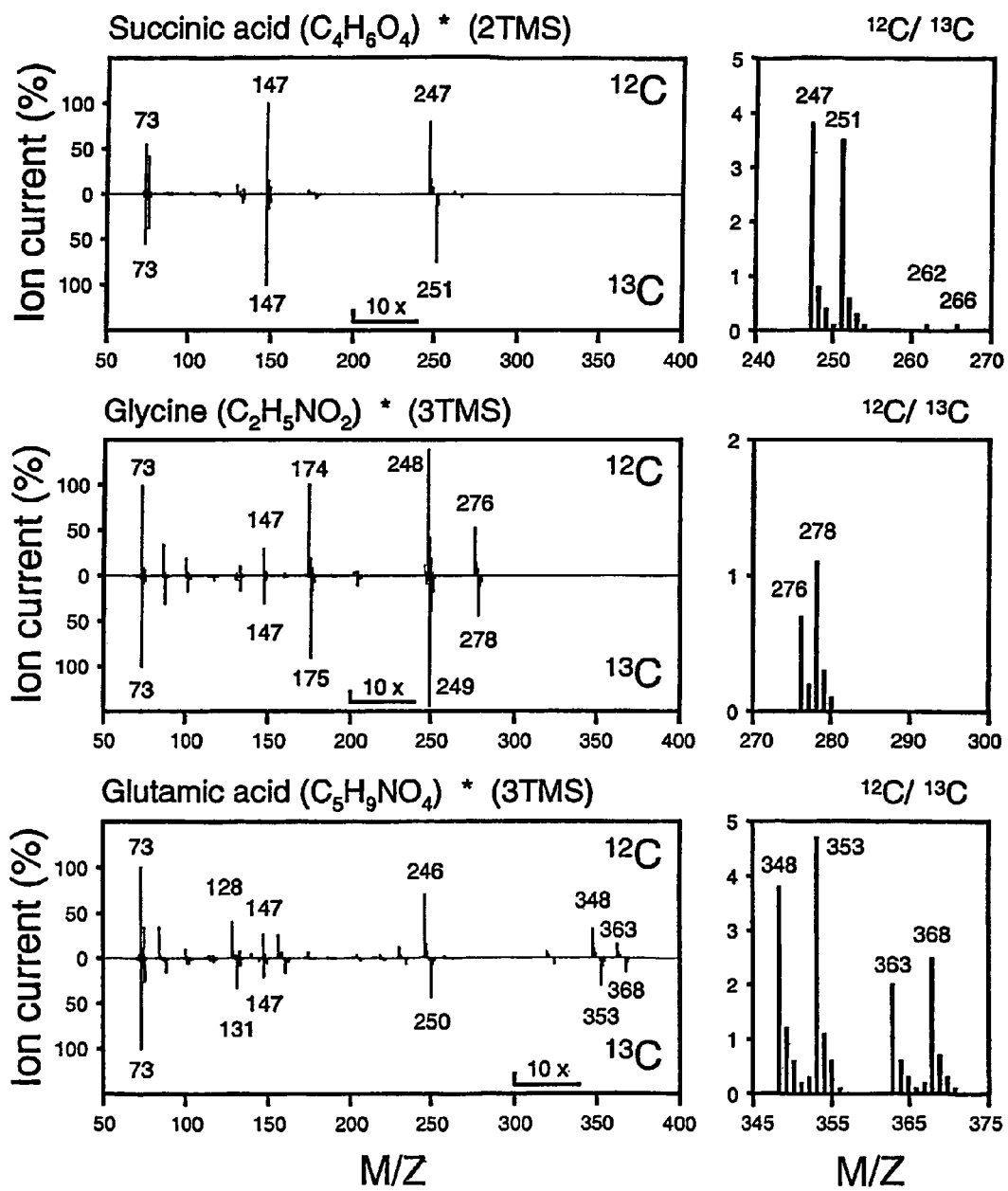

Fiehn et al., "Metabolite profiling for plant functional genomics," *Nature Biotechnology*, vol. 18, No. 11, 2000, pp. 1157-1161.

Fiehn et al., "Identification of uncommon plant metabolites based on calculation of elemental compositions using gas chromatography and quadrupole mass spectrometry," *Analytical Chemistry*, vol. 72, No. 15, Aug. 1, 2000, pp. 3573-3580.

Wagner, et al., "Construction and application of a mass spectral and retention time index database generated from plant GC/EI-TOF-MS metabolite profiles," *Phytochemistry*, vol. 62, Mar. 2002, pp. 887-900.

Allegood et al., "Use of isotopically labeled palmitate to examine de novo sphingolipid biosynthesis by LC-MS/MS: a metabolic approach," *FASEB Journal*, vol. 17, No. 4-5, Mar. 2003, Abstract No. 628.6.

Mashego et al., "MIRACLE: Mass isotopomer ratio analysis of U-$^{13}$C-labeled extracts. A new method for accurate quantification of changes in concentrations of intracellular metabolites," *Biotechnoology and Bioengineering*, vol. 85, No. 6, Mar. 20, 2004, pp. 620-628.

van Winden et al., "Metabolic Flux and Metabolic Network of *Penicillium chrysogenus* Using 2D [$^{13}$C, $^{1}$H] COSY NMR Measurements and Cumulative Bondomer Simulation," *Biotechnology and Bioengineering*, Jul. 5, 2003, pp. 75-92, vol. 83, No. 1, Wiley Periodicals, Inc.

Fiehn, "Metabolomics—the link between genotypes and phenotypes," *Plant Molecular Biology*, 2002, pp. 155-171, vol. 48, Kluwer Academic Puclishers, The Netherlands.

Christensen et al., "Metabolic Network Analysis of *Penicillium chrusogenus* Using $^{13}$C-Labeled Glucose," *Biotechnology and Bioengineering*, Jun. 20, 2000, pp. 652-659, vol. 68, No. 6, John Wiley & Sons, Inc.

Tweeddale et al., "Effect of Slow Growth Metabolite of *Escherichia coli*, as Revealed by Global Metabolite Pool ("Metabolome") Analysis," *Journal of Bacteriology*, Oct. 1998, pp. 5109-5116, vol. 180, No. 19, American Society of Microbiology.

Report dated Feb. 9, 2009 for the corresponding Canadian Patent Application No. 2,547,755. (5 pgs.).

Gaines III, et al., "Novel Nuclear Magnetic Resonance Spectroscopy Methods Demonstrate Preferential Carbon Source Utilization by *Acinetobacter calcoaceticus*", *Journal of Bacteriology*, Dec. 1996, pp. 6833-6841.

Oda, et al., "Accurate Quantitation of Protein Expression and Site-Specific Phosphorylation", *Proc. National Acad. Sc.*, vol. 96, 1999, pp. 6591-6596.

Office Action of the corresponding European Patent Application No. EP 04 804 051.3, dated Aug. 7, 2009. (4 pgs.).

Brunengraber, Henri, et al., "Applications of Mass Isotopomer Analysis to Nutrition Research", *Annu. Rev. Nutr.*, vol. 17, 1997, pp. 559-596.

Fernandez, Charles A., et al., "Correction of $^{13}$C Mass Isotopomer Distributions for Natural Stable Isotope Abundance", *Journal of Mass Spectrometry*, vol. 31, 1996, pp. 255-262.

Venters, Ronald A., et al., "Uniform $^{13}$C Isotope Labeling of Proteins with Sodium Acetate for NMR Studies: Application to Human Carbonic Anhydrase II", *Biochemistry*, vol. 30, 1991, pp. 4491-4494.

\* cited by examiner

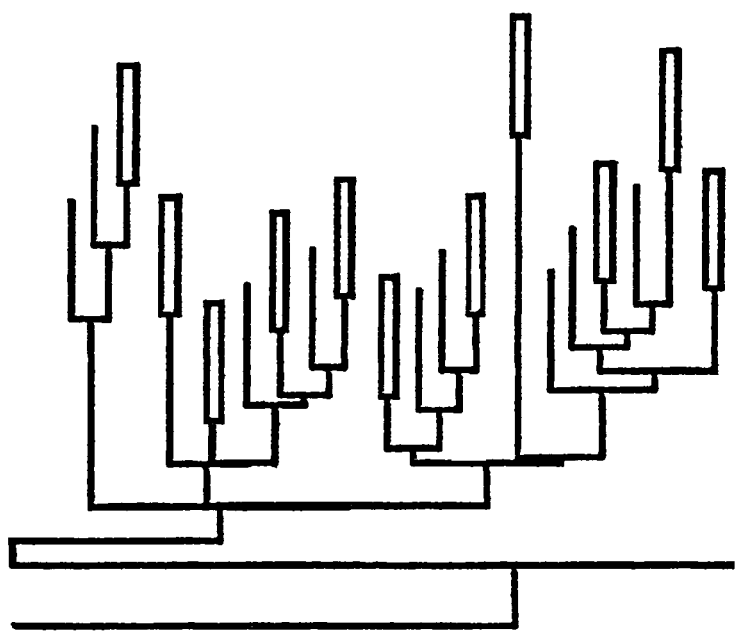
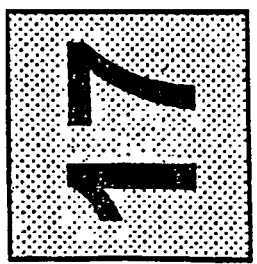
Figure 41

Figure 4A:
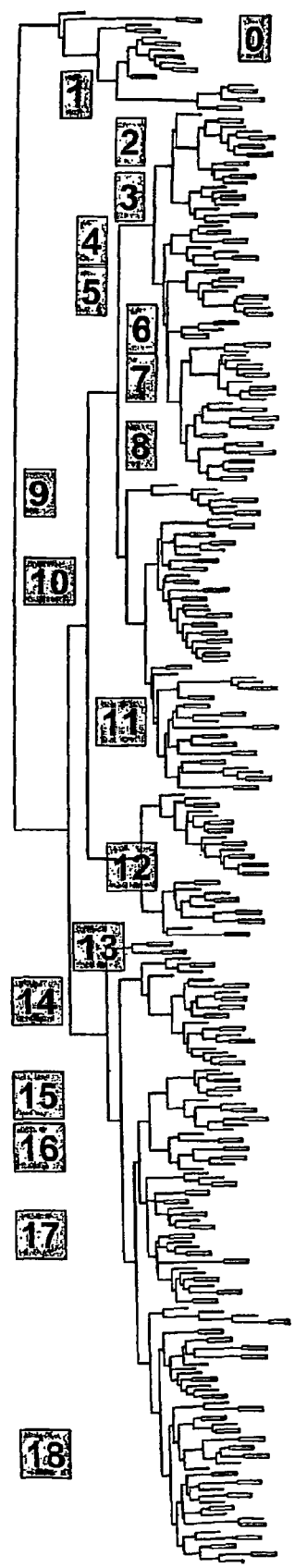
Figure 4B:
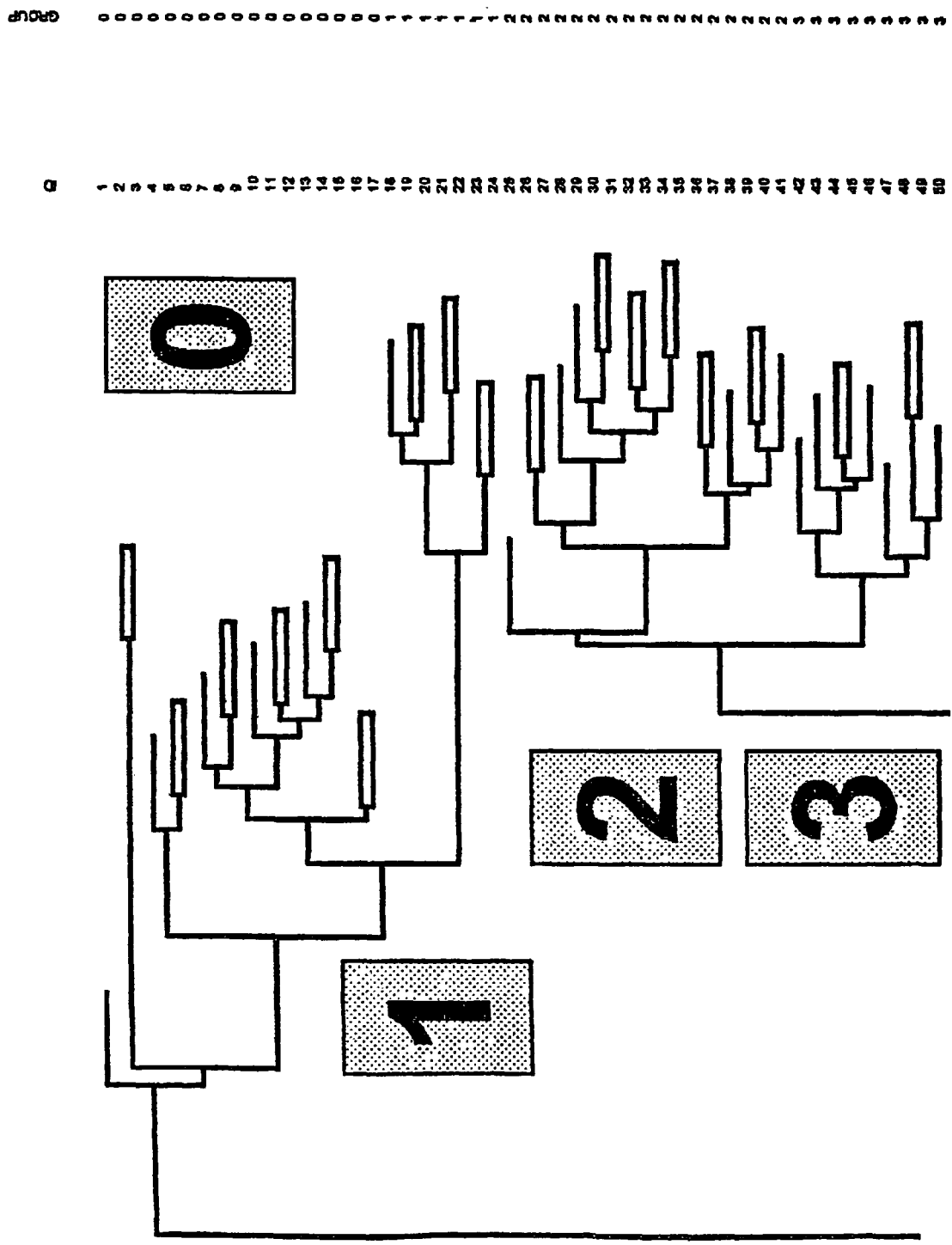
Figure 4C:
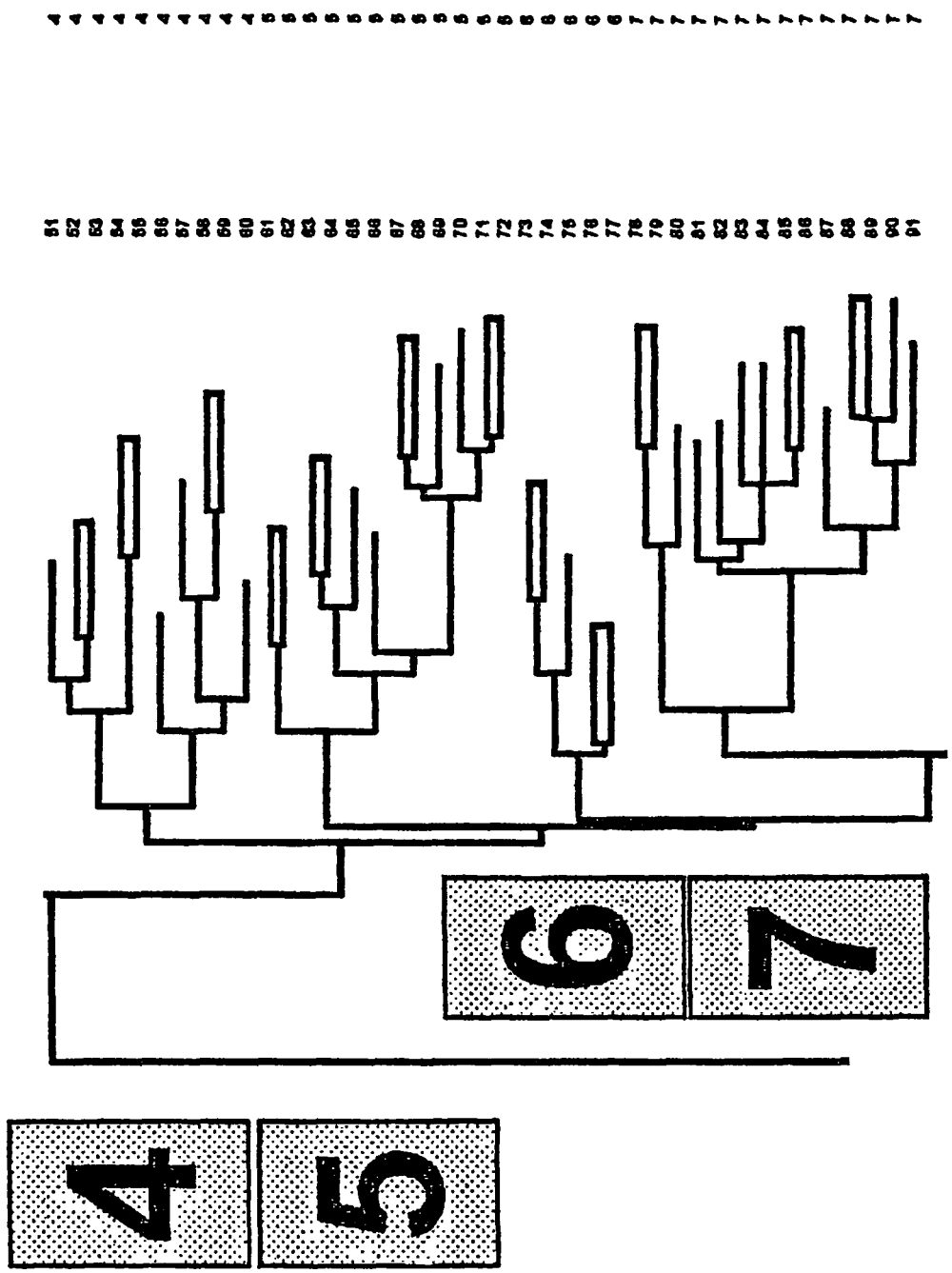
Figure 4D:
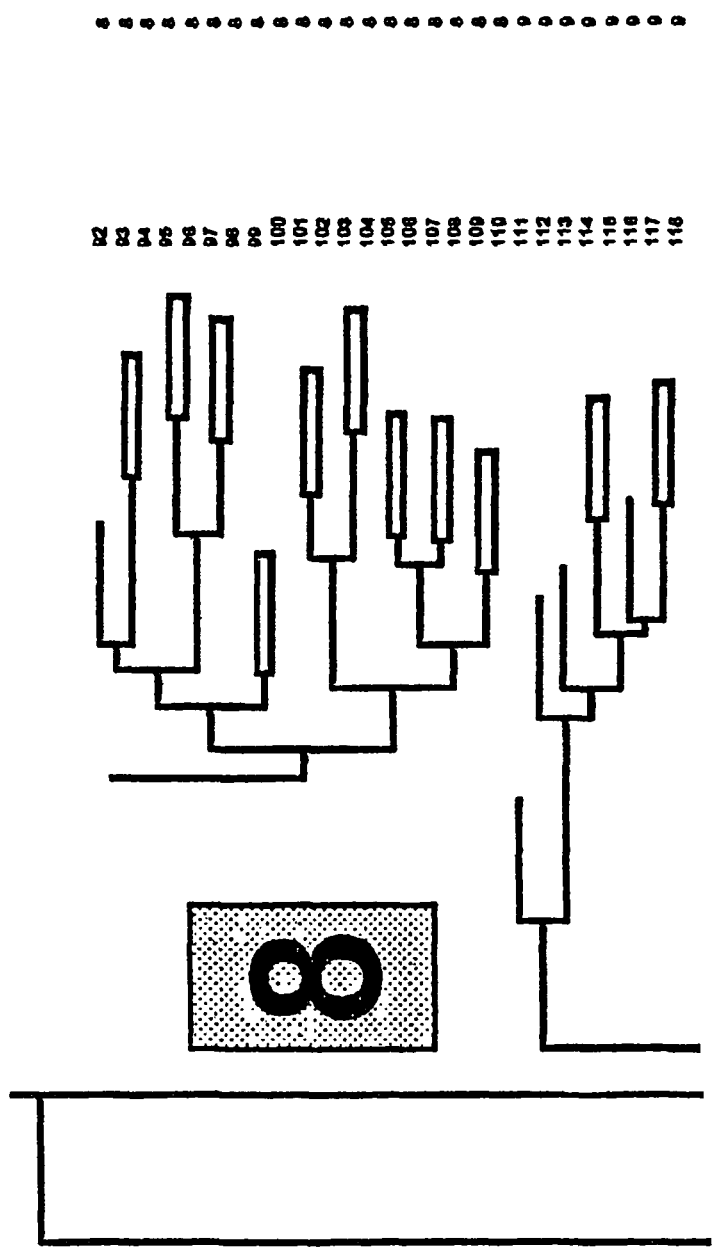
Figure 4E:
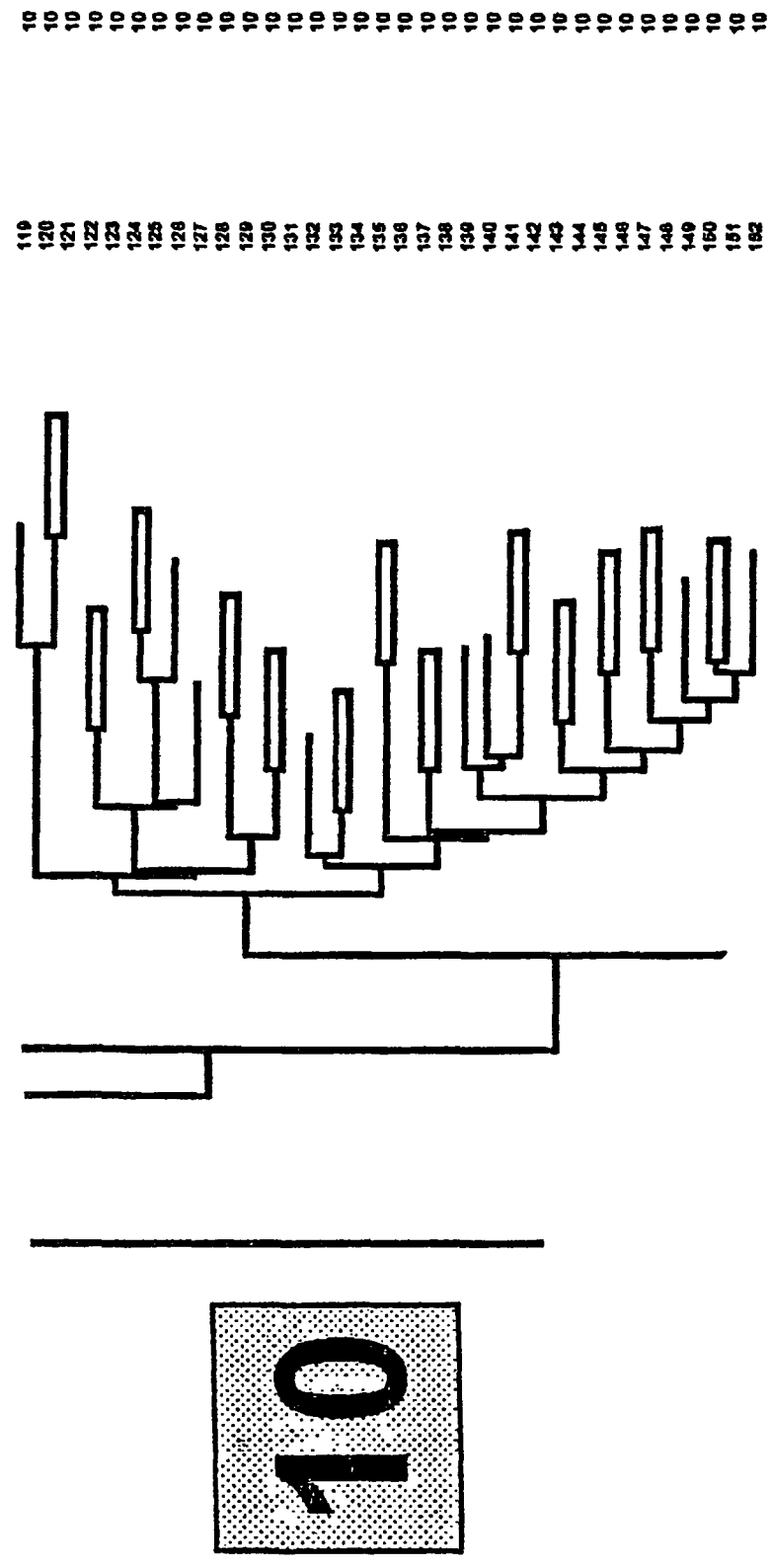
Figure 4F:
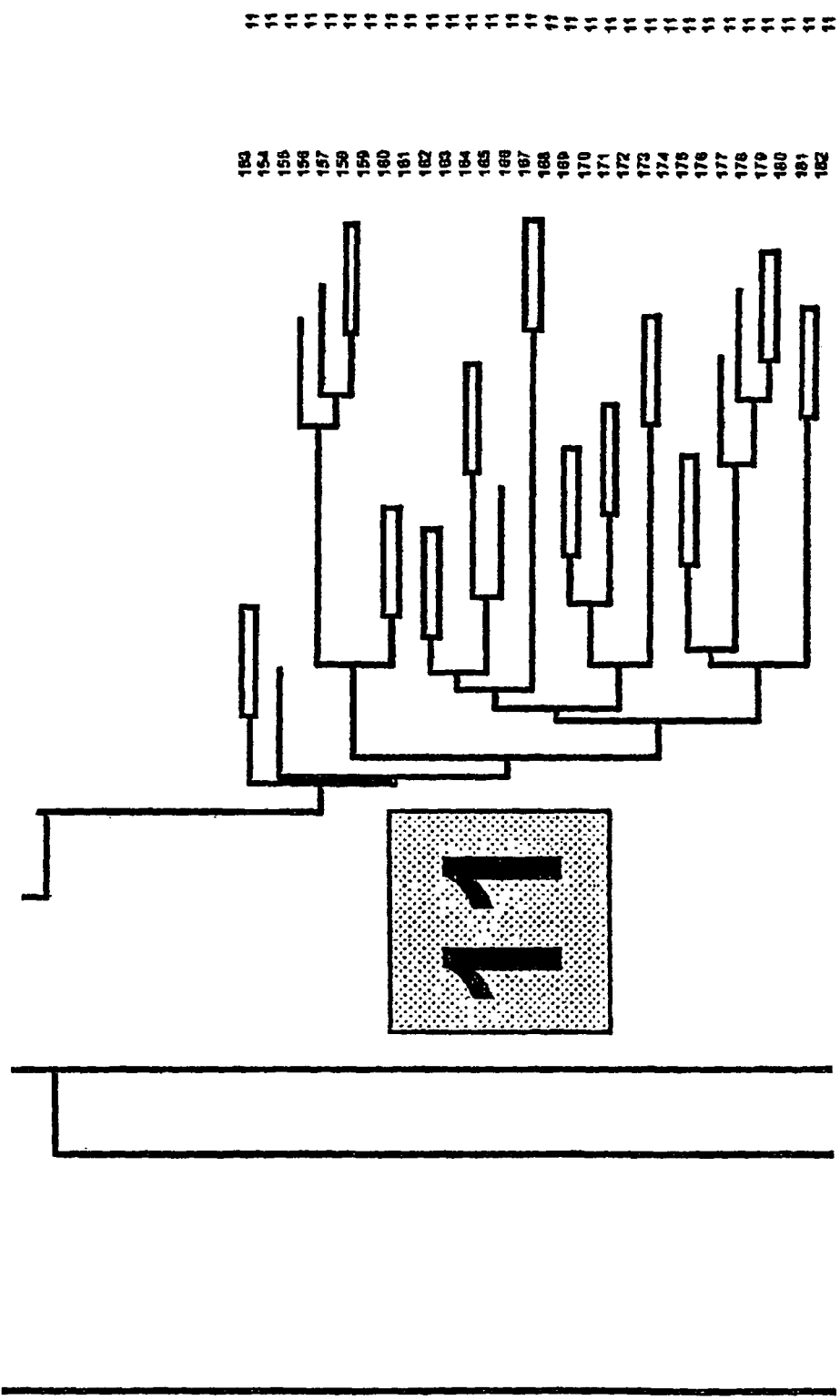
Figure 4G:
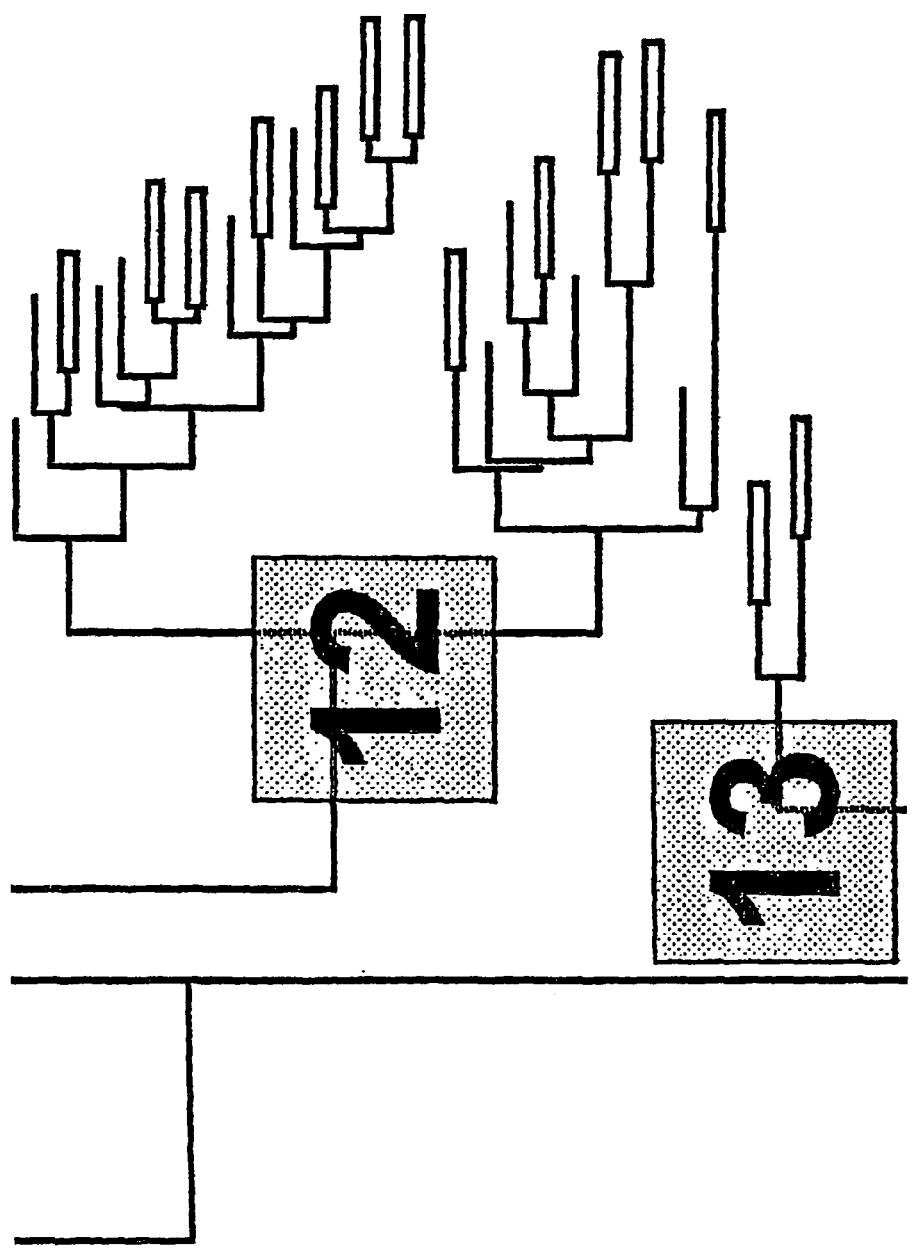
Figure 4H:
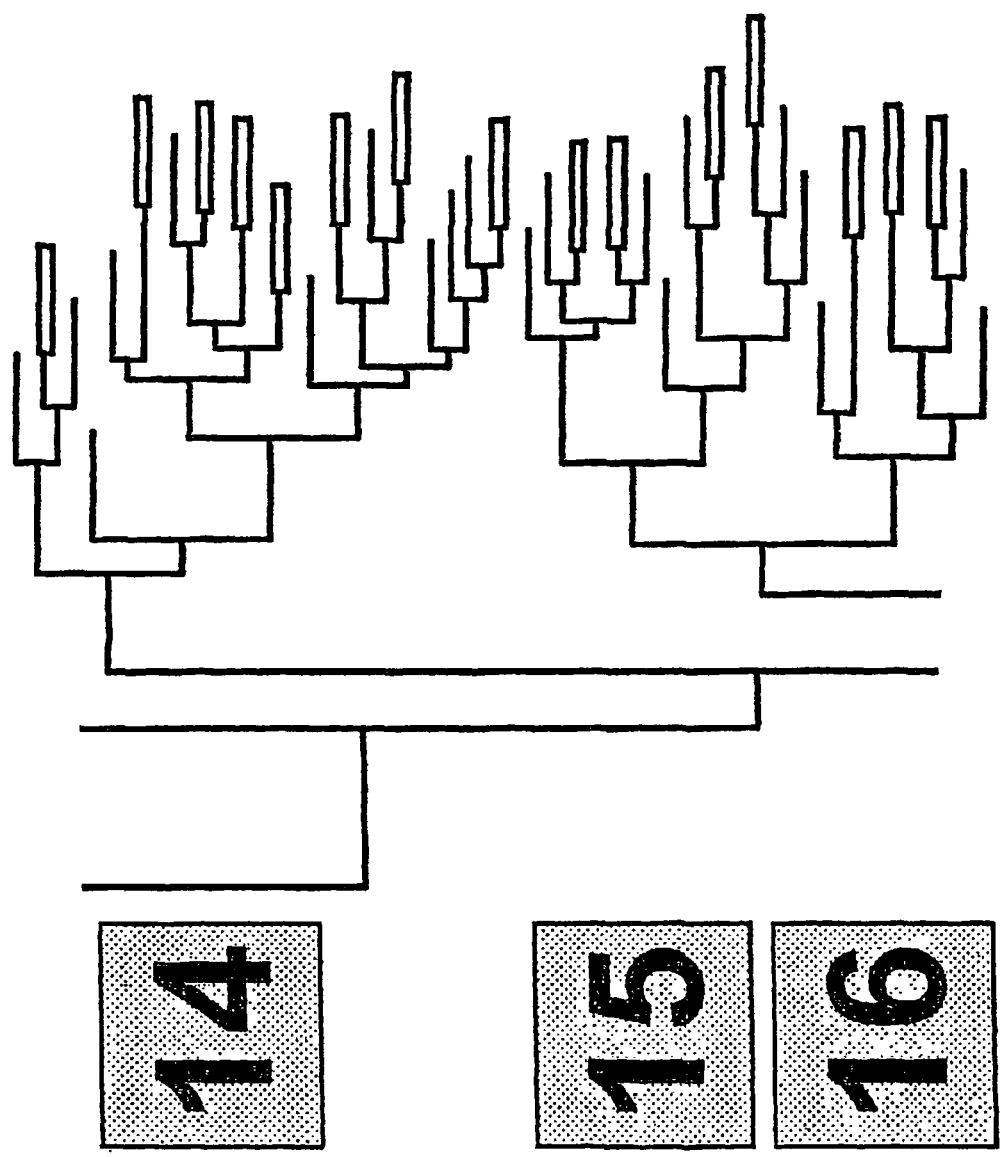

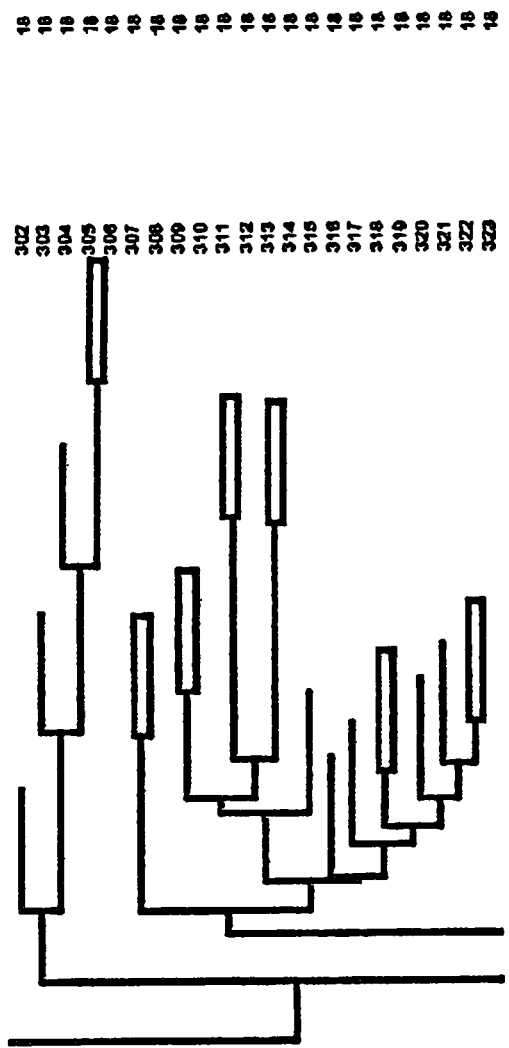
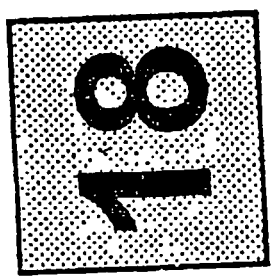
Figure 4J

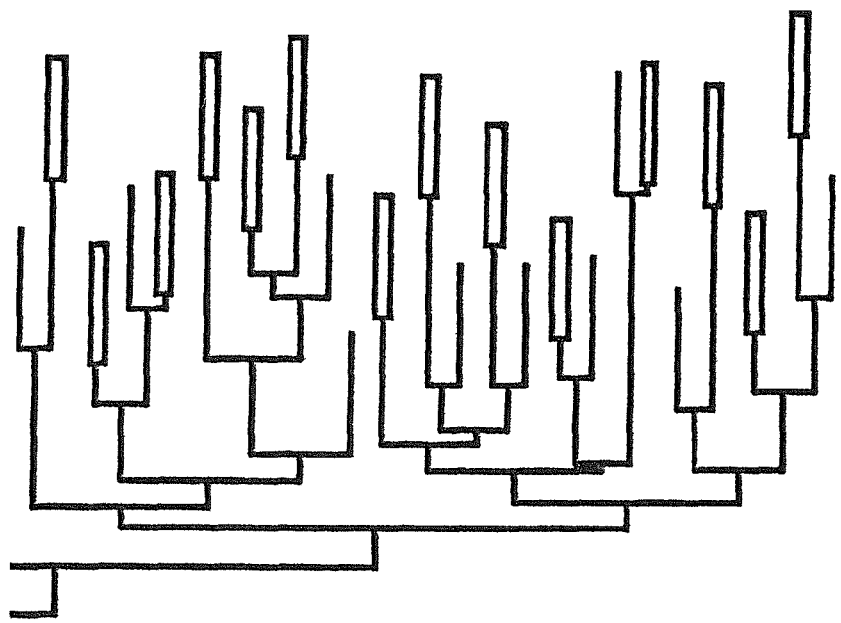
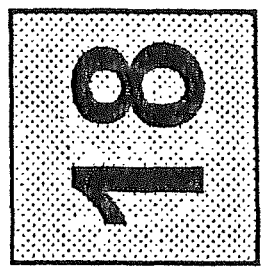
Figure 4K

METHOD FOR ANALYSING METABOLITES

The present application relates to a method for analysing the metabolites of a biological sample which comprises quantitatively determining one or more metabolites in said sample in a way that said quantitative determination resolves isotopic mass differences within one metabolite, said method being characterized in that the sample comprises or is derived from a cell which has been maintained under conditions allowing the uptake of an isotopically labeled metabolizable compound so that the metabolites in said cell are saturated with the isotope label. This method may further comprise, prior to quantitatively determining the metabolites, combining the biological sample (i.e. the first biological sample) with a second biological sample in which the metabolites are not isotopically labeled or are isotopically labeled differently from the first biological sample; and determining in said biological samples the relative quantity of metabolites which differ by their isotopical label. The present invention also relates to sets of isotopically labeled metabolites obtainable by applying this method, as well as to kits facilitating the application of this method and to corresponding uses.

The present invention belongs to the field of metabolome analyses, also referred to as metabolic profiling, i.e. the quantitative analyses of metabolites in a biological sample with the aim to investigate the state of organisms in particular with respect to biochemical regulatory networks. In the prior art, the metabolome, besides the proteome, transcriptome and genome, has become the fourth cornerstone of biological systems analyses. Only metabolome analyses allows insight into nutrient use, biosynthetic capacity of organisms, signalling and communication mediated via low molecular weight compounds and biochemical adaptive processes. Therefore profiling analyses of relative changes of all metabolites within an organism is in demand for a true biological systems analysis.

Metabolome analyses are still in early development inter alia because, in contrast to genome, transcriptome and proteome analyses, metabolome analyses has to deal with a highly diverse range of chemicals covering substances from small molecular weight volatiles up to polymers. Conventionally, different and specialised analytical platforms are used in order to analyse these different classes of compounds. Meanwhile, universally applicable analytical platforms have been developed for complex mixtures of compounds. These exploit molecular mass and chromatographic retention in so-called hyphenated technologies, like GC-MS, HPLC-MS or MALDI-TOF. Bench-top gas chromatography coupled to mass spectrometry (GC-MS) was the first technology platform proposed for large-scale metabolome analyses (Trethewey, 1999). The choice of this hyphenated technology took into regard the ideal combination of unsurpassed chromatographic separation with high selectivity, sensitivity, and dynamic range of quantitative mass detection. Moreover, both GC and electron impact ionisation (EI) mass spectrometry exhibit only minor matrix effects as compared to other MS techniques, as for example matrix assisted laser desorption/ionisation-time of flight (MALDI-TOF) (Guo, 2002) mass spectrometry or liquid chromatography coupled to mass detection (HPLC-MS) (Matuszewski, 2003). High reproducibility of the GC-MS analyses of metabolites, which routinely uses methoxyamine hydrochloride (MEOX) and N-methyl-N-(trimethylsilyl)-trifluoroacetamide (MSTFA) reagents, allowed metabolite profiling based on external quantification of respective methoxyamine (MX) and trimethylsilyl (TMS) derivatives (Fiehn, 2000a; Roessner, 2000; Roessner, 2001). The scope of metabolites covered is, however, limited (1) by the required volatility of metabolites or stable chemical derivatives of unstable metabolites, and (2) by the distribution of metabolite concentrations within each type of sample. The maximum sample load of any multi-parallel chemical analyses is determined by the predominating metabolites. GC-MS metabolite profiles have an enormous dynamic range of 4 to 5 orders of magnitude. The upper limit of quantification is set by the requirement for surplus chemical reagent and by peak deformation effects due to chromatographic overloading. Thus, biological matrices devoid of single predominant metabolites promise best potential for highly complex multi-parallel analyses (Fiehn, 2000a; Roessner, 2000).

Two main strategies are conceivable toward a more comprehensive metabolome analyses: (1) the choice of other analytical techniques which may supplement GC-MS analyses, and (2) the application of pre-fractionation and concentration techniques for the enrichment of trace compounds. However, both strategies are currently highly limited. Supplementary MS techniques, as for example MALDI-TOF-MS or HPLC-MS, are subject to strong interferences, which result from the changing compositions of complex biological matrices. These so-called matrix effects may lead even to complete suppression of ionisation and response signal (Matuszewski, 2003; Guo, 2002). On the other hand, most pre-fractionation and concentration techniques result in high or highly variable losses of metabolites.

These drawbacks preventing the use of potentially more powerful MS techniques in metabolite profiling studies may at least in part be overcome by including internal standards into the metabolite analyses. Indeed, a thorough quantitative standardisation for as many as possible measured metabolites is required. This would make it possible to extend the scope of metabolite profiling to such techniques, because it would allow an exact quantification of the metabolite levels for which a standard is available. From investigations on metabolic fluxes, it is known that metabolites can be labeled in vivo with a stable isotope (Wittmann, 2002). However, flux analyses are generally confined to the investigation of very limited biochemical pathways and do not cover metabolites in the breadth as is normally required for metabolic profiling. Consequently, the substrate compounds which are used in such studies in order to label cells with a stable isotope are typically very specific to the particular biochemical pathway to be analysed. Their production is expensive because it requires specific and time-consuming chemical syntheses.

To summarize, a practicable approach for establishing a quantitative standard for use in metabolite profiling is not in sight in the prior art. This is mainly explained by the diversity of compound classes to which metabolites may belong and by the fact that most of the metabolites cannot be tagged after extraction as it is possible for the chemically uniform transcripts and proteins (see, e.g., Gygi, 1999).

Thus, the technical problem underlying the present invention is the provision of means and methods that allow it to improve metabolome analyses by establishing a reliable quantitative standard for as many as possible metabolites in order to broaden the scope of such analyses.

This technical problem is solved by the provision of the embodiments as characterized in the claims.

Accordingly, the present invention relates to a method for analysing the metabolites of a biological sample which comprises quantitatively determining one or more metabolites in said sample in a way that said quantitative determination resolves isotopic mass differences within one metabolite, said method being characterized in that the sample comprises or is derived from a cell which has been maintained under conditions allowing the uptake of an isotopically labeled metabolizable compound so that the metabolites in said cell are saturated with the isotope with which said metabolizable compound is labeled.

The present invention is based on the experiments described in the appended Examples which show that it is possible to label substantially all possible metabolites in vivo. The proof that this principle works has been obtained by labeling yeast cells with U-$^{13}$C-glucose. This work represents the keystone to comprehensive, fully quantitative metabolome profiling and will greatly facilitate future developments within this field. It solved the technical problem of standardisation by differential labeling of metabolites with isotopes. Similar to differential labeling of transcript samples by fluorescent probes or of protein samples by chemical tagging, it is possible in the method of the present invention to tag the metabolome by saturating in-vivo labeling with isotopes. This concept can be extensively exploited for a non-biased sampling of mass spectral metabolite tags (MSTS) and isotopomer ratio (ITR) metabolite profiling. In particular, isotope-saturated extracts produced by the method of the invention may be used as a multiplex mixture of internal standards, where each component of the resulting metabolite profiles will be quantified relative to the respective fully labeled isotopomer (see Example 4 and FIG. 2). It is envisaged that these achievements, in particular the compilation of a first compendium of MSTs which, analogous to ESTs, allows qualitative assessment of the metabolome composition and the demonstration of fully quantitative ITR metabolite profiling, will greatly improve metabolome analyses.

In the prior art, isotope labeling studies are routine approaches used for metabolite flux analyses (Wittmann, 2002; Christensen (1999); Wiechert, 2001. These studies require isotopically labeled compounds, which are expensive and of limited availability. In a conventional flux experiment, a labeled compound is fed to organisms, which are pre-grown on media with ambient isotope distribution (dos Santos, 2003; Lee, 1991) resulting in the labeling of a corresponding specific isotopically labeled metabolizable compound. However, flux studies differ from the method of the invention in that they generally involve partial labeling of the metabolites of a cell. This is explained by the fact that flux studies require partial, i.e. incomplete, labeling. By contrast, the method of the present invention achieves saturating labeling which means a labeling of the metabolites as complete as possible given the degree of labeling in the isotopically labeled metabolizable compound used to label the cell from which the biological sample for analyses is derived (for more detailed definitions see below).

One advantage of the present method is the fact that it introduces an isotopic label at the site which is ideal for metabolome analyses, namely the active biological sample. In prior art technologies, a differential label is often introduced only in the course of chemical analyses such as in the currently prevailing methods for quantitative proteome (Aebersold, 2003) and transcriptome (Duggan, 1999) analyses. These technologies for example involve isotope-coded protein-tagging techniques (Gygi, 1999) and two-colour labeling by fluorescent probes (Schena, 1995; Lockhart, 1996). However, labeling only after extracting the respective compounds from the cell may introduce a bias in the labeling result. Such artefacts are excluded in the method of the invention.

Apart from incorporation of label in the course of chemical analyses, there has been at least one approach to label proteins in vivo. Oda (Proc. Natl. Acad. Sci. USA 96 (1999), 6591-6596) describe whole cell-labeling for proteome analyses using the stable isotope $^{15}$N. However, in vivo isotope labeling of the entire set of metabolites has not been reported in the prior art. In particular, by using $^{13}$C-labeling of yeast cultures, the present invention demonstrates that combined mass spectral analyses of differentially labeled samples, especially $^{13}$C-ITR profiles, can be generated. In particular, the experiments underlying the present invention surprisingly show that complete (i.e. saturating) labeling of metabolites could be achieved in yeast cells. The results obtained in the appended Examples are surprising because it could not have been excluded that carbon sources other than the isotopically labeled metabolizable compound (in the examples U-$^3$C-glucose) which are present in the medium could have prevented an efficient broad isotope labeling of the metabolites. It is almost impossible to avoid in the medium the presence of such other carbon sources like for instance essential nutrients, such as vitamins, or auxotrophic markers. The processing of these compounds in the cultured cells could have severely interfered with isotope labeling and thereby prevented the required saturating labeling. However, as is shown in the Example experiments, the lack of labeling in the cell due to the presence of the unlabeled carbon sources in the medium is greatly restricted to the compounds themselves or to direct metabolic products thereof (see Example 1). A mixing of label with unlabeled compounds essentially did not take place. This was surprising and means that in vivo labeling with isotopes can indeed be applied for achieving broad coverage of the metabolites with isotopic labeling.

Another surprising finding was that the presence of isotope label in the metabolites does not substantially influence the distribution of metabolite levels in the sample when it is compared with a metabolite profile obtained from a corresponding unlabeled sample (i.e. a sample, wherein the cells have been fed with nutrients in which the isotopes are present in the naturally occurring, i.e. ambient proportions). This is for example evident from the results depicted in FIG. 2 and described in Example 4. This could not have been expected since it is known that enzymes may discriminate between isotopomers. For instance, such effects are described from plant physiology such as for RUBISCO, $CO^2$-fixation and phosphoenolpyruvate carboxylase (PEPC) (see, e.g., Le Roux-Swarthout, J. Plant Physiol. 157 (2000), 489-493) and from fungi, yeast or other microorganisms, e.g., for, pyruvate decarboxylase (PDC), and the isoprenoid metabolizm (see, e.g., Stivers, Biochem. 32 (1993), 13472-13482; Henn, Appl. Environ. Microbiol. 66 (2000) 4180-4186; Londry, Appl. Environ. Microbiol. 69 (2003), 2942-2949). Thus, it was reasonable to expect that, caused by isotope discrimination, the labeling of metabolites with isotopes would influence the distribution of metabolite levels in the biological sample. But, as it is shown herein, the isotopically labeled metabolites show a distribution that greatly corresponds to that obtained for unlabeled metabolites. This proves suitability of the method of the invention for standardizing metabolite analyses.

The experimental results summarized in the following show that the method of the invention may become an indispensable tool for the future development of metabolite profiling.

Figure 9:
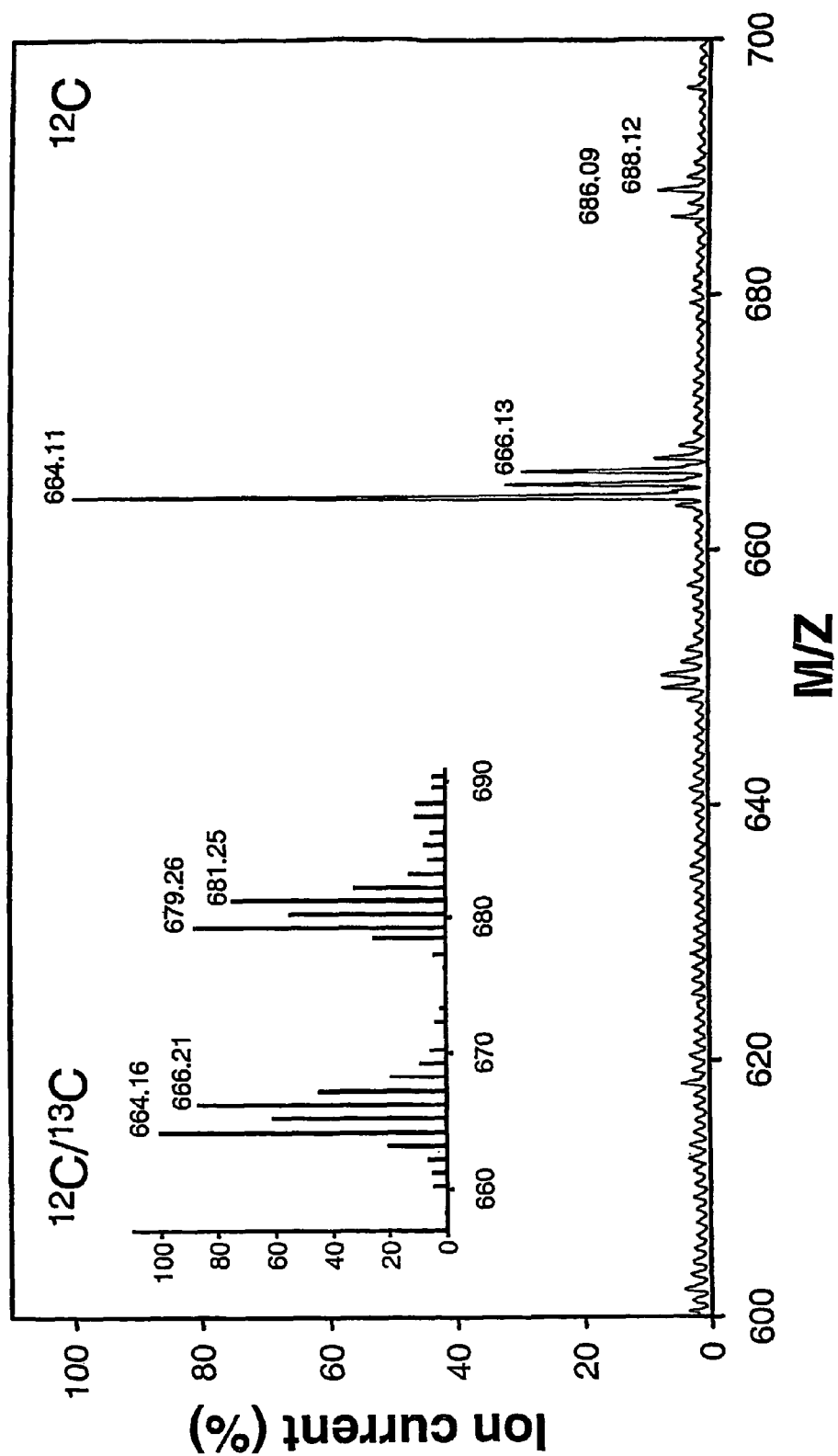

The present invention is herein exemplified in experiments using a *Saccharomyces cerevisiae* model which was subjected to saturating in vivo stable isotope labeling by growing on an exclusive $^{13}$C-source (see, e.g., FIGS. 1 and 9). The in vivo labeling of metabolites in yeast generates isotopomer tags which could be differentially detected by mass spectrometry. When applied as internal quantitative standard, isotope-labeled compounds may facilitate a meaningful quantitative analyses if for example two samples, the one being saturatingly labeled and the other not being labeled (i.e. having ambient isotope abundances) are compared and the relative ratio between each isotopomer tag and the corresponding unlabeled metabolite is determined. Interestingly, this working principle may even facilitate those mass spectral technologies such as MALDI-TOF-MS which are prone to matrix suppression effects and high variability and which therefore hitherto were not applied for quantitative metabolite profiling analyses. An example of successfully using the method of the invention by applying MALDI-TOF-MS is presented herein (Example 9 and FIG. 9). This means that the method described herein may allow to extend multi-parallel metabolite profiling in principle at least to all mass spectrometry-based technologies.

A further advantage of the method of the invention over conventional metabolome analyses is that it allows an immediate proof of the metabolic origin of any mass spectral tag which is detected in biological samples. While protein and mRNA sequence diversity provides information about the source species by the sequence information contained therein, the origin is not immanent in metabolite structure per se, except for the subset of species-specific secondary metabolites. However, as soon as a pair of labeled and non-labeled MSTs is found, chemical artefacts or laboratory contaminations can immediately be ruled out.

In addition, mass shifts allow a direct insight into the number of carbon atoms present within each compound or fragment. This property of the method of the invention increases the insight into the chemistry of those MSTs the chemical nature of which is unknown and may support the identification of MSTs by other techniques (Table 3).

In analogy to expressed sequence tags (ESTs), identfied and non-identified MSTs may be used as a highly useful tool to characterise the metabolome of any biological sample. Again in analogy to tools for sequence comparison, MSTs can easily be identified by matching of mass spectral fragmentation and chromatographic retention. Furthermore, clustering technologies allow a meaningful classification of MSTs (FIG. 4) (Wagner, 2003).

Figure 6:
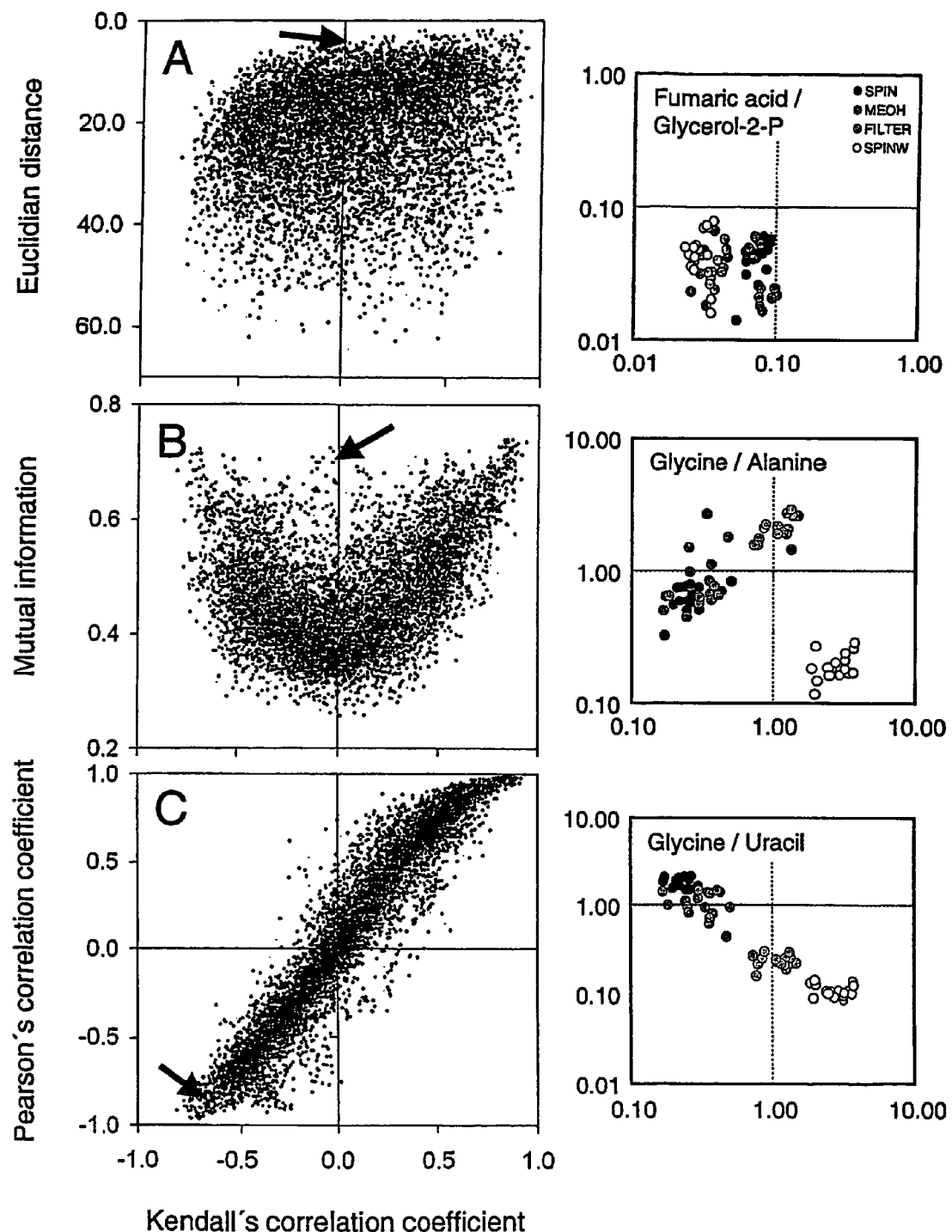

As a further advantageous property, the method of the invention allows a fast investigation of the precision of analytical methods which are being developed for metabolite profiling. In addition, it makes quantitatively standardized metabolome analyses accessible to biological samples which are obtained by pre-purification and enrichment of fractions of the total metabolite extract taken from a biological sample, for instance in order to detect trace metabolites. In the prior art, such samples fall below the detection limits of conventional GC-MS profiling. The possibility of the method of the invention to quantitatively determine minor amounts of metabolites facilitates to conduct metabolite co-response analyses which may provide direct information about quantitative metabolite interactions in biological systems. Such interactions may be expected based on theoretical considerations (Steuer, 2003). Observed metabolite co-responses may be uncoupled or may follow linear functions. Metabolite co-response may be either constitutive or conditional with respect to the set of experiments under investigation. In Example 8, metabolite co-response analyses applying the method of the invention are described. Accordingly, metabolite co-responses may best be discovered and judged by a set of different distance measures, among which the Euclidian distance is least indicative (FIG. 6). Metabolite interactions may reflect canonical pathway definitions (FIG. 7), but may also allow to discover cross-pathway interactions (FIG. 8). Investigations into these interactions are highly valuable, because they can provide insights into common mechanisms of metabolic control. However, to date, such analyses are restricted due to the limited coverage of metabolome data. Based on the extension of metabolite data mining that is now possible by applying the method of the invention, for instance because of the possibility to exploit MALDI-TOF for quantitative determination of metabolite levels on a broad scale, it is conceivable that the present invention will further the development of quantitative metabolome analyses, in particular towards trace compounds and general co-factors.

As it is explained above, the present invention belongs to the field of the metabolic profiling or metabolome analyses. This means that the method of the invention is of use for quantitatively determining one or more metabolites in a biological sample. The term "quantitative determining" refers to the determination of the relative or absolute amount of each analyzed metabolite in the sample. Generally, such a determination leads to a so-called metabolite profile pertaining to the respective biological sample. Such metabolite profiling approaches have been carried out in many laboratories and therefore belong to the prior art.

Since isotopic labeling is applied in the method of the invention, it is necessary that the technique used to quantitatively determine the metabolites resolves isotopic mass differences as they may occur within one metabolite. Compounds that differ from one another only by one or more isotopes incorporated into the chemical structure are generally referred to as "isotopomers". The technique used to detect the metabolites must therefore be capable of discriminating between two compounds that differ in their mass by as little as one relative atomic mass. Corresponding techniques are known to the skilled practitioner and described in the literature. They involve different kinds of mass spectrometry or NMR, as is described in further detail further below.

The term "isotopic labeling" is to be understood to refer to compounds that are labeled with an isotope that is not the main isotope of the element of said isotope. "Labeled" means in this context to have a significantly and, for detection purposes, usefully increased proportion of the label-isotope as compared to the abundance of said isotope occurring in nature, preferably the proportion of the label-isotope is increased to at least 80%, more preferably to at least 90% and even more preferably to at least 95% and most preferred to at least 99% of the total of all isotopes of the respective element. The term "isotopic labeling" furthermore preferentially refers to compounds in which the label-isotope is present in the above-mentioned proportion at each possible position within the chemical structure of the compound. However, partial labeling of compounds may also be of use in the context of the present invention. Such applications require that means of correction for the proportion of residual non-labeled isotopomers are applied. In this case, labeling needs to be saturating, i.e. the proportions of isotopomers for each metabolite needs to be constant in the labeled sample, so that the isotopomer proportions can be determined in a control experiment and used for mathematical correction of the metabolite profiling results. Preferably, the isotopically labeled metabolizable compound used in order to label the cell contains of the respective element only the label-isotope (in the proportion that is technically feasible) as it is the case with U-$^{13}$C-glucose where all six carbon atoms are the $^{13}$C isotope.

The method of the present invention is characterized in that the sample comprises or is derived from a cell which has been maintained under conditions allowing the uptake of an isotopically labeled metabolizable compound so that the metabolites in said cell are saturated with the isotope with which said metabolizable compound is labeled.

It is a critical feature of the method of the invention that the metabolites are saturated with the isotopic labeling. "Saturated" (or "saturating labeling") means that the metabolites in the cell or the biological sample derived therefrom contain an amount of isotope label that substantially corresponds to the amount of label in the metabolizable compound taken up by the cell in order to label it, and that substantially all of the metabolites to be analyzed contain the isotope label. In particular, "saturating labeling" refers to an amount of labeling of the metabolites to be analyzed so that these metabolites overall contain at least 50%, preferably at least 70%, more preferably at least 80%, still more preferably at least 90% and most preferably at least 95% of the amount of isotopic label as present in the isotopically labeled metabolizable compound. The term "substantially all of the metabolites to be analyzed contain the isotope label" means that at least 70%, preferably at least 80%, more preferably at least 90%, still more preferably at least 95% and most preferably at least 98% of the metabolites to be analyzed are labeled, i.e. differ by at least one relative atomic mass from the corresponding unlabeled counterpart. Preferably, substantially all of the metabolites to be analyzed contain the isotope label if at least 20, more preferably at least 50, still more preferably at least 100, even more preferably at least 150 and most preferably at least 200 or even at least 300 metabolites of the biological sample to be analyzed contain the isotopic label.

Exceptions to the labeling to saturation may be tolerated, however, should be taken into account when analysing the metabolite data obtained. Non-labeled metabolites may be present in the biological sample when, in addition to the isotopically labeled metabolizable compound, other compounds, for example essential nutrients like metabolizable compound, other compounds, for example essential nutrients like vitamins or auxotrophy markers, have been provided to the cell via the culture medium and these compounds do not contain the isotope label. Therefore, it may happen that cells which are labeled to saturation contain unlabeled metabolites which are these other compounds or metabolic products thereof.

The number and selection of metabolites analyzed in the method of the invention depends on the goal to be achieved by carrying out the method of the invention. It is typical for metabolic profiling like the method of the invention to aim at quantitatively determining an as large as possible subset of metabolites in order to obtain as much as possible metabolite data. Here, the possibility to label in principle each metabolite by the method of the invention is a big advantage over prior art approaches because it provides a quantitative standard for each metabolite to be analyzed.

Accordingly, in a preferred embodiment of the method of the invention, at least 20, more preferably at least 50, still more preferably at least 100, even more preferably at least 150 and most preferably at least 200 or even at least 300 metabolites are quantitatively determined.

The term "metabolite" refers to any substance within a cell or produced by a cell, including secreted substances, which can be quantitatively determined by applying the method of the invention, that is for which suitable techniques for determining the amount are available. Preferably, these substances are not macromolecules (i.e. biopolymers) such as DNA, RNA or proteins. Particularly preferred are metabolites with a low molecular weight preferably the metabolites have a molecular weight of not more than 4000 Da, preferably not more than 2000 Da, more preferably not more than 1000 Da. Typically, the metabolites to be analyzed may belong to the following, non-limiting list of compounds: carbohydrates (e.g. sugars, oligo- and polysaccharides such as polyglucans as for example starch or polyfructans), sugar alcohols, amines, polyamines, amino alcohols, aliphatics, aliphatic alcohols, amino acids, lipids, fatty acids, fatty alcohols, organic acids, organic phosphates, organic ions, other inorganic ions bound to metabolites, nucleosides, nucleotides, sugar nucleotides, purines, pyrimidines, such as adenine and uracil, sterols, terpenes, terpenoids, flavons and flavonoids, glucosides, carotenes, carotenoids, cofactors, ascorbate, tocopherol, vitamins, polyols, organic amines and amides such as ethanol amine and urea and/or heterocyclic compounds such as nicotinic acid.

As is evident from the appended Examples, the method of the invention also involves analysing metabolites of which the chemical nature is unknown. However, metabolites (herein also referred to as "mass spectral metabolite tags" or "MSTs") of unknown chemical nature may nevertheless provide informative data on the biological sample analysed. It is clear that, if a metabolite of unknown chemical nature is revealed by carrying out the method of the invention to have an interesting property or diagnostic value or characteristic behaviour, this metabolite may be further characterized by applying suitable analytical methods known in the art.

In a particularly preferred embodiment, the method of the invention refers to the quantitative determination of metabolites comprising sugars, sugar alcohols, organic acids, amino acids, fatty acids, vitamins, sterols, organic phosphates, polyamines, polyols, nucleosides, purines, pyrimidines, adenine, uracil, organic amines and amides such as ethanol amine and urea and/or heterocyclic compounds such as nicotinic acid.

The isotope used for in vivo labeling in connection with the present invention may be selected among available isotopes that may be suitable for applying the method of the invention. As a preferred selection, a skilled person may use an isotope for which corresponding isotopically labeled metabolizable compounds are available, in particular commercially available. As a further preferred choice, isotopes for use in the method of the invention should be such that they do not harm viability of the cells from which the biologically sample for analyses is taken Or that they do not interfere with the metabolizm such as by influencing the activity of metabolic enzymes. In this regard, it is thus preferred to use stable isotopes rather than radioactive ones. As a further aspect, one should take into account that elements such as carbon or hydrogen are preferred over elements that are present in metabolites more rarely in order to cover the metabolites of a cell by in vivo labeling as completely as possible. Particularly preferred isotopes are $^{13}C$, $^{15}N$, $^{18}O$ and $^{2}H$, with particular preference of $^{13}C$.

The label-isotope is incorporated into the cells from which the biological sample for analyses is taken by maintaining the cell under conditions allowing the uptake of said compound. This means that the compound should be one that is readily taken up by the cells and that is also readily metabolized so that it is ensured that saturation with the isotopic label can be achieved. Depending on the kind of cells or organism to be labeled, the label may for example be provided by feeding cultured cells such as yeast cells or mammalian cells with a nutrient, e.g. a carbon source if the label is $^{13}C$. If the cells to be labeled are within a multicellular organism, the label may be incorporated by subjecting the labeled metabolizable compound through the substrate (e.g. the water) if it is a plant or by injecting the labeled compound into it if the organism is an animal, for instance a vertebrate, in particular a mammal.

As the isotopically labeled metabolizable compound, substances should be used that provide for an effective uptake of the label by the cell. Preferably, the compound may be totally labeled with the isotope (i.e. no atom of the respective element in the compound is of another isotope than the label-isotope). Corresponding labeled compounds may be available from commercial suppliers such as those mentioned in the Examples. Particularly preferred isotopically labeled metabolizable compounds are U-$^{13}$C-glucose, $^2$H$_2$O, H$_2$$^{18}$O, U-$^{13}$C acidic acid, $^{13}$C carbonate and $^{13}$C carbonic acid.

The term "biological sample" encompasses any amount of material comprising cells or derived from a cell that is susceptible to the method of the invention. In the present context, the term "cell" refers to any conceivable living entity that is capable of being in vivo-labeled according to the teachings of the present invention. Accordingly, the method may be applied to any type of cell, prokaryotic or eukaryotic cells, viral particles, wild-type or transformed, transduced or fused cells, or derivatives thereof such as membrane preparations, liposomes and the like. The cells may furthermore be part of a tissue, an organ or a complete organism such as a plant or an animal. The cells may be in a naturally occurring form or in a man-made form such as in a cultured form, e.g. cell culture, protoplast culture, tissue culture or the like.

The term "derived" used in connection with characterizing the biological sample means any kind of measures a skilled person may apply in order to modify the labeled cells or the direct environment of the cells, wherein the "direct environment" is characterized by the presence of at least one metabolite produced by the cells, in order to prepare a sample for use in quantitatively determining the metabolites contained therein by applying the method of the invention. Such measures may for example involve typical sample preparation or extraction techniques common to those skilled in the art. The direct environment may for example be the extracellular space around a cell, the apoplast, the cell wall, the interstitial space or the culture medium. Furthermore, the biological sample derived from a cell may be a certain part of the cell, for example certain cellular compartments such as plastids, mitochondria, the nucleus, vacuoles etc. In a preferred embodiment of the present invention, the biological sample comprises yeast cells or plant cells.

A "biological sample" in the context of the present invention can for instance be fresh material such as a tissue explant, a body fluid or an aliquot from a bacterial or cell culture, preferably deprived of the culture medium, that may be directly subjected to extraction. On the other hand, samples may also be stored for a certain time period, preferably in a form that prevents degradation of the metabolites in the sample. For this purpose, the sample may be frozen, for instance in liquid nitrogen, or lyophilized. The samples may be prepared according to methods known to the person skilled in the art and as described in the literature. In particular, the preparation should be carried out in a way suitable to the respective detection technique applied. Furthermore, care should be taken that the respective compounds to be analyzed are not degraded during the extraction process. Biological samples for metabolite analyses may for example be prepared according to procedures described in Roessner (2000).

In a further preferred embodiment, the method of the invention further comprises fractionating or purifying the biological sample so that the sample contains a subset of the metabolites contained in the cell from which the sample is derived.

By this additional fractionation and/or purification step, it is for example possible to select low abundant metabolites out of the whole pool of metabolites whereby, without this step, these metabolites might not be detectable for example because their signals are superimposed with strong signals of highly abundant metabolites. In prior art metabolite profiling methods, such a fractionation or purification would cause the loss of the quantitative relationship to other metabolites which would render the quantification of low abundant metabolites nearly impossible. This problem has been overcome by the present invention since the isotopically labeled metabolites serve as a quantitative standard that may be co-fractionated/-purified with the non-labeled metabolites.

The fractionation and/or purification may be carried out according to standard procedures known in the art. It is clear that preferably procedures should be used that do not or at least only to a low tolerable degree change the distribution of the metabolites in the sample.

The quantitative determination of metabolites in a biological sample may be carried out by any known suitable method that can resolve mass differences within one metabolite. This may involve various nuclear magnet resonance (NMR) and mass spectrometry (MS) techniques that are known to a person skilled in the art, whereby mass spectrometry is preferred in the context of the present invention. Different suitable NMR and MS techniques are for instance described in Wittmann (Adv. Biochem. Engin. Biotechnol. 74 (2002), 39-64) and Szyperski (Q. Rev. Biophys. 31 (1998), 41-106). Preferred set ups for MS techniques for use in the present invention involve the combination of MS with gas chromatography (GC) as it is routinely used in state-of-the-art metabolite analyses, such as GC-MS described in the appended Examples.

In cases of ambiguous fragment interpretation, analyses using GC-MS-MS or corresponding MS tandem arrangements may support the identification of isotopomer fragment pairs. For example, GC-MS systems supplied with ion trap technology allow the selection of individual primary fragments and subsequent secondary mass spectral fragmentation (Birkemeyer, 2003; Mueller, 2002). These MS-MS mass spectral fingerprints may allow an unequivocal identification of corresponding primary ions.

The determination of the amount of metabolites of interest can be done according to well-known techniques known in the prior art and familiar to the person skilled in the art. Preferably, techniques are applied that allow the identification and quantification in one step and, advantageously, are suited to record the respective metabolites contained in the sample in a comprehensive manner.

Further methods for quantitatively determining the metabolites for use in accordance in the present invention include liquid chromatography/mass spectrometry (LC/MS), the use of radioactivity in connection with suitable methods known to the skilled person, thin layer chromatography (TLC), capillary electrophoresis (CE), direct injection MS, flow injection MS, MS/MS, MS/MS/MS, and further combinations of MS steps (MSn), fourier transform ion mass spectrometry (FT/MS), gel permeation chromatography (GPC), TLC, CE, HPLC, GPC, any other chromatographic or electrophoretic technique or any mass spectrometric technique which is hyphenated in-line or off-line to mass spectrometry. If appropriate, any of the above methods may be combined.

An exemplary non-biased analyses is described in Fiehn (2000b). In this study, of different plant mutants, 326 distinct compounds (ranging from primary polar metabolites to sterols) were detected and relatively quantified, including both identified and non-identified compounds, by applying GC/MS analyses. Another example of a GC/MS analyses that can be applied in the method of the invention has been described by Roessner (2001), Where it was used for comprehensively studying the metabolizm in potato tubers.

In a particularly preferred embodiment of the method of the invention, the mass spectrometry used is matrix-assisted laser desorption ionisation/time-of-flight (MALDI-TOF) mass spectrometry.

This embodiment makes use of the surprising finding that the saturating in vivo labeling achieved by the method of the invention makes it possible to obtain quantitative metabolite profile data.

It is furthermore preferred that the method of the invention as described hereinabove involves that the metabolites are chromatographically separated prior to quantitative determination.

This preferred embodiment refers to the chromatographic separation which has already been described above by referring to the particularly preferred example of using gas chromatography in settings such as GC-MS or GC-MS-MS. Other suitable chromatography methods such as HPLC, RP-HPLC, ion-exchange HPLC, GPC, capillary electrophoresis, electrophoresis, TLC, chip-base micro-fluidic separation, affinity-interaction chromatography using antibodies or other ligand-specific binding domains may also be used in this regard.

In another preferred embodiment, the method of the invention further comprises the step of introducing external standards for one or more of the quantitatively determined metabolites.

The introduction of external standards or standard dilution series allows the determination of metabolite concentrations in absolute terms. By contrast, embodiments of the method of the invention in which no external standards or standard dilution series are applied allow the exact quantification in relative terms, i.e. concentration changes observed relative to reference quantities as observed in experimental control samples. The introduction of external standards and the provision of such standards may be carried out as described in the literature and as is known by the person skilled in the art.

As has been mentioned above, the method of the invention includes the quantitative determination of metabolites the chemical nature of which is yet unknown. Accordingly, in a preferred embodiment, this method further comprises the step of identifying one or more of the metabolites which are quantitatively determined. This identification may be carried out by analytical methods known to the skilled practitioner and described in the literature.

In a particularly preferred embodiment, this identification comprises identification by secondary fragmentation.

Secondary fragmentation techniques may be carried out by methods known in the prior art; in particular by GC-MS-MS or other $MS^n$ techniques. Separate recording and subsequent comparison of chemical intermediates from MS-MS fragmentation pathways of, e.g., $^{13}C$ isotopomer pairs is highly facilitated by providing the number of carbon atoms present within each observed MS-MS fragment.

In an especially preferred form of this embodiment, identification of the metabolites comprises electron impact ionisation, MS-MS technology and/or post source decay analyses of molecular ions or fragments.

Such techniques are known to a person skilled in the art. In particular, post source decay analyses may be carried out as is described in Example 9 using NADH detection as an example.

In a further preferred embodiment, the method of the invention as described above may be carried out in such a way that the cell to be labeled has been maintained under conditions additionally allowing the uptake of an isotopically unlabeled metabolizable compound and said compound and/or metabolic products thereof are quantitatively determined. Preferably, the uptake of the unlabeled compound takes place when the cell is already saturated with the isotopic label.

Preferably, this embodiment involves comparing the amount determined for the isotopically unlabeled metabolizable compound and/or said metabolic products thereof with the amount obtained by carrying out said method correspondingly, but without the uptake of said unlabeled metabolizable compound.

Figure 2B:
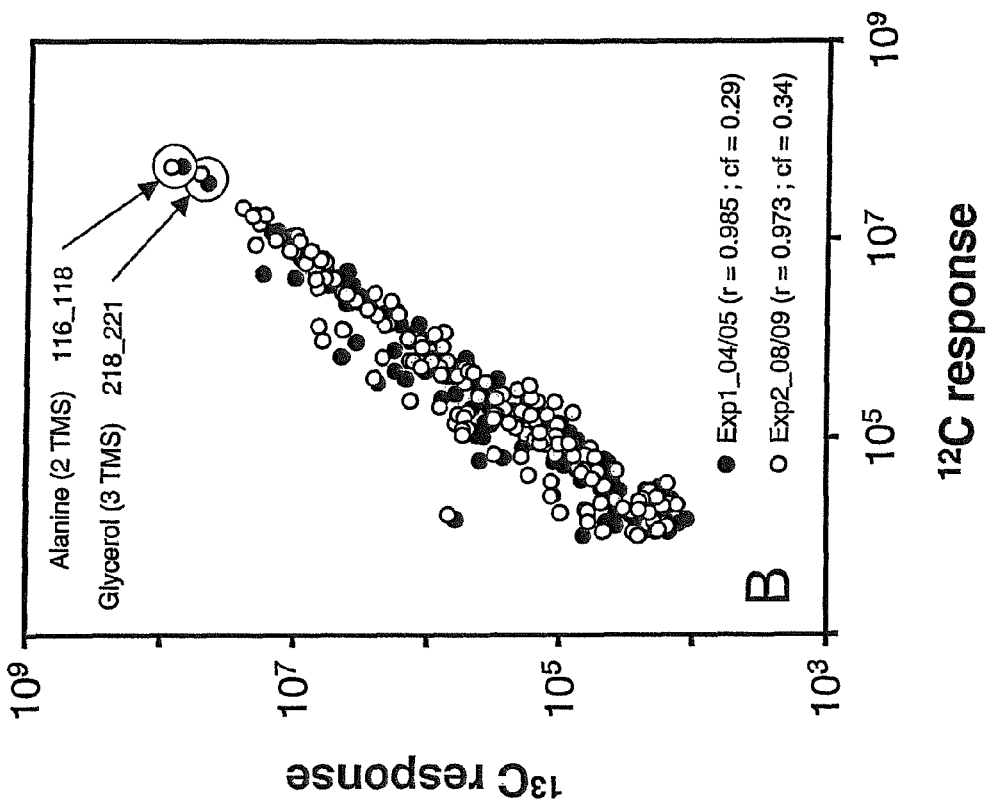
Figure 2A:
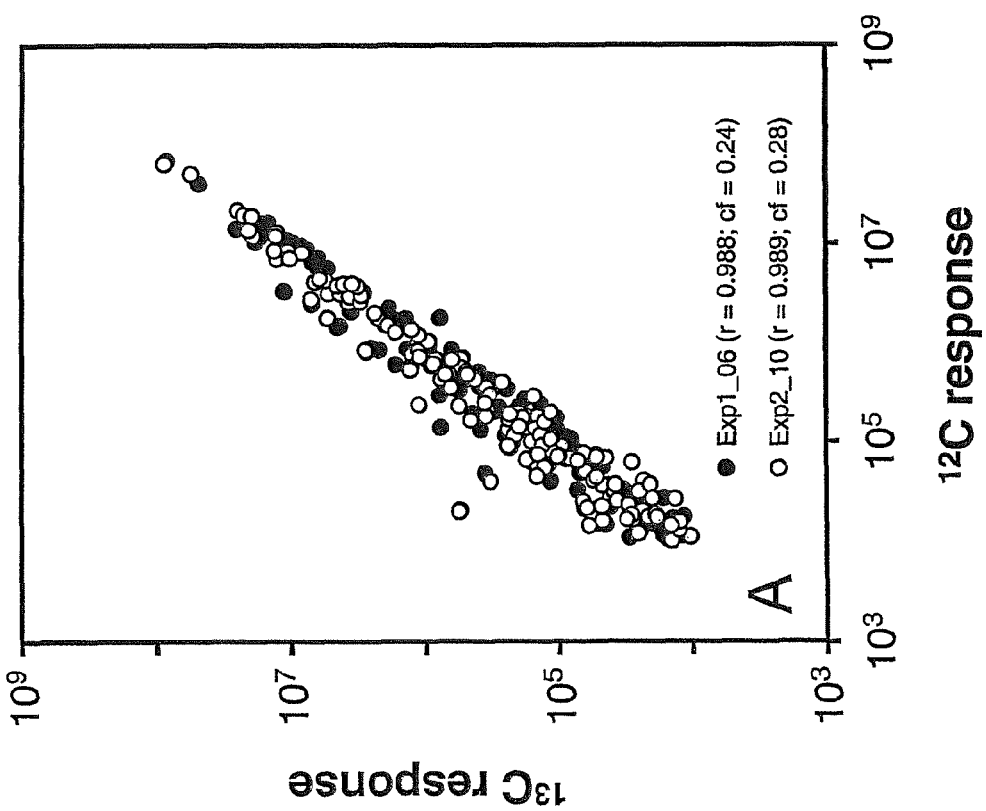

The present preferred embodiment relates to an application of the present invention which is also referred to as "inverse labeling". This term refers to an inversion of conventional flux studies (see, e.g., Wittmann, Adv. Biochem. Engin. Biotechnol. 74 (2002), 39-64) in which a labeled metabolite is added to a cell and its fate is traced in order to analyse metabolic pathways. The present preferred embodiment of the invention appears to be feasible because of the high similarity of metabolite profiles from ambient $\delta^{13}C$- and $^{13}C$-saturated yeast cultures (FIG. 2A, B). Moreover, in Example 2, a corresponding experiment is described in which L-lysine was added in unlabeled form to the culture medium after the yeast cells reached saturated $^{13}C$-labeling. In a further experiment, the enrichment of the non-labeled trace compound nicotinic acid and the incorporation of this moiety into NAD(H) within a $^{13}C$-saturated yeast metabolome was shown (Example 9).

The present embodiment allows it to achieve results similar to those obtained in conventional flux studies. It allows to utilize the relatively inexpensive supply of substances with ambient $\delta^{13}C$ composition for biochemical pathway elucidation within the background of a $^{13}C$-saturated metabolome. But it has the advantage that the specific metabolite the metabolization of which shall be analysed does not need to be provided in labeled form, which often is considerably expensive. Rather, in the method according to the present embodiment, the metabolite to be investigated can be used in the cheaper unlabeled form. A further advantage is the increased versatility of this approach as compared to conventional flux studies since virtually every possible metabolite can be tested for or even more than one metabolite, without being dependent on the availability of the metabolite(s) in labeled form.

In a further preferred embodiment of the above-described method of the invention, one or more proteins and/or transcripts in said sample(s) is/are quantitatively determined and analysed, in addition to metabolites.

This embodiment refers to one of the main aspects in systems biology which aims at combining metabolome data with data obtained from transcriptome and/or proteome analyses in order to obtain a comprehensive pictures of regulatory mechanisms in biological systems. In this context, it is evident that the method of the present invention may, be combined with methods that quantitatively determine transcripts and/or proteins from the same biological system, in particular organism or cells, of which the metabolites are quantitatively analysed in accordance with the method of the invention. Transcriptome and proteome analyses as well as mathematical evaluation and correlation analyses of the data may be conducted by methods described in the prior art. It is contemplated that, preferably, the transcriptome and/or proteome analyses conducted in combination with the metabolome analyses according to the present invention may also benefit from the advantages of in vivo labeling. Thus, if the quantitative determination of transcripts or proteins is done by suitable techniques such as mass spectrometry the transcripts or proteins may be isotopically labeled just as the metabolites and thereby also be used as a quantitative standard.

It is particularly preferred that the preferred embodiment is carried out in such a manner that said metabolites and proteins and/or transcripts are each determined from the same biological sample.

This particularly preferred embodiment is based on a technology described in WO 03/058238 and in Fiehn (Eur. J.

Biochem. 270 (2003), 579-588). The method described therein provides data useful for quantitatively analyzing metabolites, proteins and/or RNA in a biological source material, whereby said analyses involves suitable statistical evaluation and correlation analyses on the data obtained. In this method, extracting, identifying and quantifying of at least two compound classes of the group consisting of metabolites, proteins and RNA are each determined from one sample. Accordingly, in the present particularly preferred embodiment, the sample preparation in order to quantitatively determine metabolites and proteins and/or transcripts is carried out by applying the corresponding teachings of WO 03/058238. Thereby, it is especially preferred that (i) the metabolites are extracted from the sample with at least one solvent or mixture of solvents; and (ii) the RNA is extracted from the remainder of the sample after step (i). Thereby, it is a further option that metabolites may additionally be extracted from the yet undissolved remaining cellular material contained in the sample after step (ii). Preferably, extraction is carried out by using a mixture of solvents that comprises at least one highly polar solvent, at least one less polar solvent and at least one lipophilic solvent, advantageously a mixture of solvents comprising water, methanol and chloroform. More preferably, this mixture of solvents contains water, methanol and chloroform in the approximate proportion by volume of 1:2.5:1. Advantageously, the extraction in step (i) is carried out at a temperature between −60° C. and +4° C.

As a further preferred embodiment of the present invention, the method as described hereinabove further comprises, prior to quantitative determining the metabolites, combining the biological sample (i.e. the first biological sample) with a second biological sample in which the metabolites are not isotopically labeled or are isotopically labeled differently from the first biological sample; and determining in said biological samples the relative quantity of metabolites which differ by their isotopical label.

Preferably, the second biological sample is not isotopically labeled.

By this preferred embodiment, the method facilitates the quantification of metabolite data which hitherto was only possible by using external metabolite samples as quantitative standards. Here, the in vivo labeled metabolites present the quantitative standard for the metabolites of the second biological sample. This allows the correlation analyses of a wide set of metabolites of two biological samples which correspond to two different phenotypic and/or genotypic states of the cells from which the biological samples are derived.

Accordingly, in a specifically preferred embodiment, the first and the second biological sample correspond to different phenotypic and/or genotypic states of the cells comprised in the samples or from which the samples are derived.

By applying this embodiment of the method of the invention, it is possible to find correlations between the difference in the phenotypic and/or genotypic state and changes in the metabolite profile for instance by performing metabolite co-response analyses.

The term "phenotypic state" refers to differences in the phenotype of the cell under investigation or the organism in which it resides. "Phenotype" means any kind of feature that can be detected and which is not a feature of the genome. Such phenotypic states may for example be visually identifiable such as a morphological or anatomical difference like they can be observed at different developmental stages. Phenotypic states may likewise manifest themselves by the composition of chemical compounds or the occurrence of a disease. Thus, the phenotypic states may for instance be a healthy state in comparison to one or more pathogenic states, different stages of a pathogenicity or an uninfected versus one or more infected organisms. The term "genotypic state" reflects differences in the genome of the cells under investigation. Thus, if the samples are taken from different genotypic states of a cell, the term "cell" specifically refers to cells according to the definition given above which belong to the same taxonomic unit, but which differ in at least one genetic trait. Specifically, the "taxonomic unit" is a genus, preferably a species, and more preferably an even lower taxonomic rank such as a race, variety, cultivar, strain, isolate, population or the like. Most preferably, the taxonomic rank is an isogenic line with variance in only a limited number, preferably three, more preferably two genetic traits and most preferably one genetic trait, whereby "genetic trait" refers to a chromosomal region, a gene locus or, as it is preferred, to a gene. Typically, differences in the genotypic state can be differences between a wild-type organism and one or more corresponding mutant or transgenic organisms or between different mutant or transgenic organisms. A certain genotypic state may be stable or transient as is the case with transduced or transfected cells, for instance containing a plasmid, phage or viral vector. Advantageously, organisms of different genotypic state are analyzed when they are in the same developmental stage.

It is immediately clear that the terms "phenotypic" and "genotypic" states may overlap. In particular, normally a genotypic state, if the differing genetic trait(s) is/are expressed in the organism, lead(s) to a difference in the phenotype.

According to the above explanations, in a preferred embodiment of the method of the invention, the different phenotypic and/or genotypic states are different developmental stages, environments, nutritional supplies, taxonomic units, wild-type and mutant or transgenic genomes, infected and uninfected states, diseased and healthy states or different stages of a pathogenicity.

In a further preferred embodiment of the method of the invention as described hereinabove, said analysing further involves suitable statistical evaluation and correlation analyses of the data obtained and, optionally, network analyses.

This refers to any mathematical analyses method that is suited to further process the quantitative data provided by the method of the invention. This data represents the amount of the analyzed metabolites present in each sample either in absolute terms (e.g. weight or moles per weight sample) or in relative terms (i.e. normalized to a certain reference quantity).

Quantitative analyses involves suitable statistical evaluation and correlation analyses. The former includes normalization to the total content of the respective compounds, correction of background levels and the combination of the data sets obtained from different experiments (if more than one sample is analysed) into a single data sheet. Corresponding mathematical methods and computer programs are known to the skilled practitioner. Examples include SAS, SPSS and systatR. As the next step, the statistically pre-treated data may be subjected to a pairwise correlation analyses. Here series of pairs of data points from the analyzed compounds are looked at for correlation, whether positive or negative, for instance using Pearson's correlation coefficient.

In a preferred embodiment, the quantitative analyses referred to in the method of the invention furthermore involves network analyses. Network analyses aims at finding out higher order interplays of multiple factors on the basis of pairwise correlation data. If, according to one of the above-described preferred embodiments, metabolites and transcripts and/or proteins are quantitatively determined, the obtained several data sets, preferably each obtained from one sample, correlations between metabolites and proteins and/or transcripts as well as within these classes of compounds can be analyzed in order to derive information about the network regulation of biological systems, e.g. upon genetic or environmental perturbation. A comprehensive overview of methods for quantitatively analyzing data obtained according to the method of the invention including principle component analyses, "snapshot analyses", Pearson correlation analyses, mutual information and network analyses can be found in Fiehn (2001).

In a further aspect, the present invention relates to a set of isotopically labeled metabolites obtainable from a sample which comprises or is derived from a cell which has been maintained under conditions allowing the uptake of an isotopically labeled metabolizable compound so that the metabolites in said cell are saturated with the isotope with which said metabolizable compound is labeled.

The present invention also relates to such cells which can be cells as described above in connection with the method of the invention.

As is explained hereinbefore, the isotopically labeled metabolites obtained from a biological sample in accordance with the method of the present invention may be used as a quantitative standard for the quantitative determination of the metabolites of a second biological sample. Thus, a set of these labeled metabolites is also an object of the present invention. Preferably, this set can be used to standardize results of a metabolome analyses conducted with the same species of cells as that from which the set of metabolites is obtained. However, it is also feasible that this set may be of use to standardize metabolite data obtained from a different species. This would generally require that metabolites of the set are identical with metabolites of the second biological sample. Identity can be determined or confirmed by using methods known in the art and described herein. For instance, the in vivo isotopically labeled metabolites obtained from yeast may be used as a quantitative standard for metabolites of plant cells since, for a considerable subset of each of these metabolites, the metabolites overlap such as the metabolites of the primary metabolic pathways.

As a further use of the set of isotopically labeled metabolites of the invention, or corresponding cells containing them, it is envisaged that the set or the cells can be used as a qualitative standard in order to identify metabolites from a second, unlabeled biological sample.

The set of metabolites may be prepared in accordance with the above explanations for carrying out the method of the invention. For the purposes of storing and transporting that set, corresponding methods may be applied which are suitable in order to ensure that degradation of each kind of metabolite contained therein is at least minimized to a tolerable degree and which are known to a person skilled in the art.

In a further embodiment, the present invention refers to the use of the set of isotopically labeled metabolites mentioned above as a quantitative standard for determining the amount of one or more metabolites in a biological sample.

Furthermore, the present invention relates to a kit comprising an isotopically labeled metabolizable compound and a manual for use in carrying in out the method of the invention or the set of isotopically labeled metabolites described above.

The components of the kit of the invention may be packaged in containers such as vials in a storable and transportable form. If appropriate, one or more of said components may be packaged in one and the same container.

Additionally, the present invention relates to the use of an isotopically labeled compound that can be metabolized by a cell for labeling the metabolites in said cell in a saturating manner.

Such uses may be carried out in accordance with the above-outlined explanations for the method of the invention.

The present invention also relates to the use of an isotopically labeled compound that can be metabolized by a cell for the quantitative determination of metabolites in a biological sample comprising or being derived from said cell.

Such uses may be carried out in accordance with the above-outlined explanations for the method of the invention.

Likewise, the present invention relates to the use of an isotopically labeled compound that can be metabolized by a cell for analysing the metabolite profile of a biological sample comprising or being derived from said cell.

Such uses may be carried out in accordance with the above-outlined explanations for the method of the invention.

These and other embodiments are disclosed and encompassed by the description and examples of the present invention. All of the publications, patents and patent applications referred to in the specification in order to illustrate the invention are hereby incorporated by the reference in their entirety. Further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nim.nih.gov/PubMed/medline.html. Further databases and addresses, such as http://www.ncbi.nim.nih.gov/, http://www.infobiogen.fr/, http://www.fmi.ch/biology/research_tools.html, http://www.tigr.org/, are known to the person skilled in the art and can also be obtained using, e.g., http://www.google.de. An overview of patent information in biotechnology and a survey of relevant sources of patent information useful for retrospective searching and for current awareness is given in Berks, TIBTECH 12 (1994), 352-364.

Furthermore, the term "and/or" when occurring herein includes the meaning of "and", "or" and "all or any other combination of the elements connected by said term".

The present invention is further described by reference to the following non-limiting figures, tables and examples.

THE FIGURES AND THE TABLES SHOW

FIG. 1 shows the results of head-to-tail analyses of electron impact ionisation mass spectra of yeast metabolites extracted from GC-MS metabolite profiles.

The yeast metabolites succinic acid, glycine and glutamic acid were trimethysilylated prior to GC analyses. The number of silylated functional groups and the magnification factor of the high molecular mass range is indicated. Head-to-tail mass spectra are from separate GC-MS analyses of ambient $\delta^{13}$C- and $^{13}$C-saturated yeast extracts. Insets to the right show the M$^+$ and [M-15]$^+$ fragment ranges of combined $^{13}$C-isotopomer ratio (ITR) metabolite profiles. The isotopomer [M-15]$^+$ fragment pairs of succinic acid (2TMS), glycine (3TMS), and glutamic acid (3TMS) are M/Z 247_251, M/Z 276_278, and M/Z 348_353. Glutamic acid (3TMS) exhibited abundant molecular ions, M$^+$, M/Z 363_368.

FIG. 2 depicts a comparison of ITR metabolite profiling (A, C) and conventional metabolite profiling (B,D).

Selected ion responses of $^{12}$C- and $^{13}$C-isotopomer fragment pairs, which represent the same substance from ambient $\delta^{13}$C- and $^{13}$C-saturated yeast extracts (A, B), and fragments which represent the same isotopomer in two different experiments (Exp1 and Exp2) from either the ambient $\delta^{13}$C or $^{13}$C-saturated yeast culture (C, D) are plotted. ITR was performed in two GC-MS analyses (06, 10), whereas four GC-MS analyses were required for conventional metabolite profiling (ambient $\delta^{13}C$: 04, 08; $^{13}C$-saturated: 05, 09). Pearson's linear correlation coefficients (r) and average coefficients of variation (cf) are shown in the insets.

Figure 3:
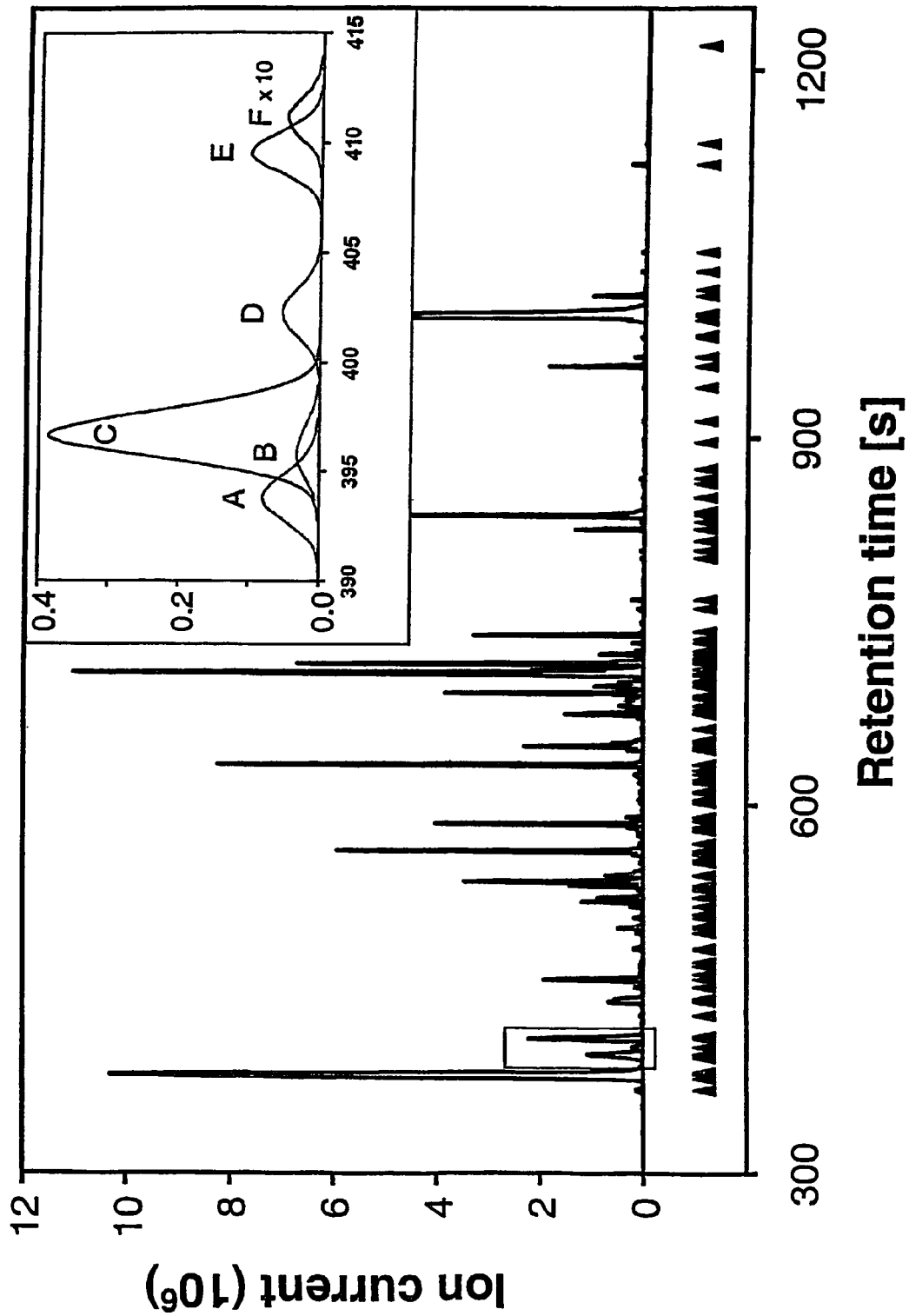

FIG. 3 represents a GC-TOF-MS metabolite profile of yeast strain BY4741. Ticks below the total ion current trace of the main profile indicate the automated deconvolution of mass spectral components with $S/N \geq 100$ which were performed by Pegasus chromatography data processing software. The inset shows selected ion traces of deconvoluted components from the shaded area of the main profile. A isoleucine (2TMS), M/Z=158; B threonine (2TMS), M/Z=117; C proline (2TMS), M/Z=142; D glycine (3TMS), M/Z=174; E 2,2,3,3-d4-succinic acid (2TMS), M/Z=251; F succinic acid (2TMS); M/Z=247 (factor of magnification 10). The presence of 2,2,3,3-d4-succinic acid resulted from standard addition of a deuterated isotopomer.

FIG. 4 depicts a clustering tree of identified, and non-identified MSTs from extracts of *Saccharomyces cerevisiae* strain BY4741 and pure standard compounds. MSTs were classified into groups by hierachical clustering of a complete symmetric matrix of pair-wise mass spectral match values (Table 4). 18 groups of MSTs were classified at a cut-off at approximately 50% diversity (the MST groups are described in Example 6).

Figure 5:
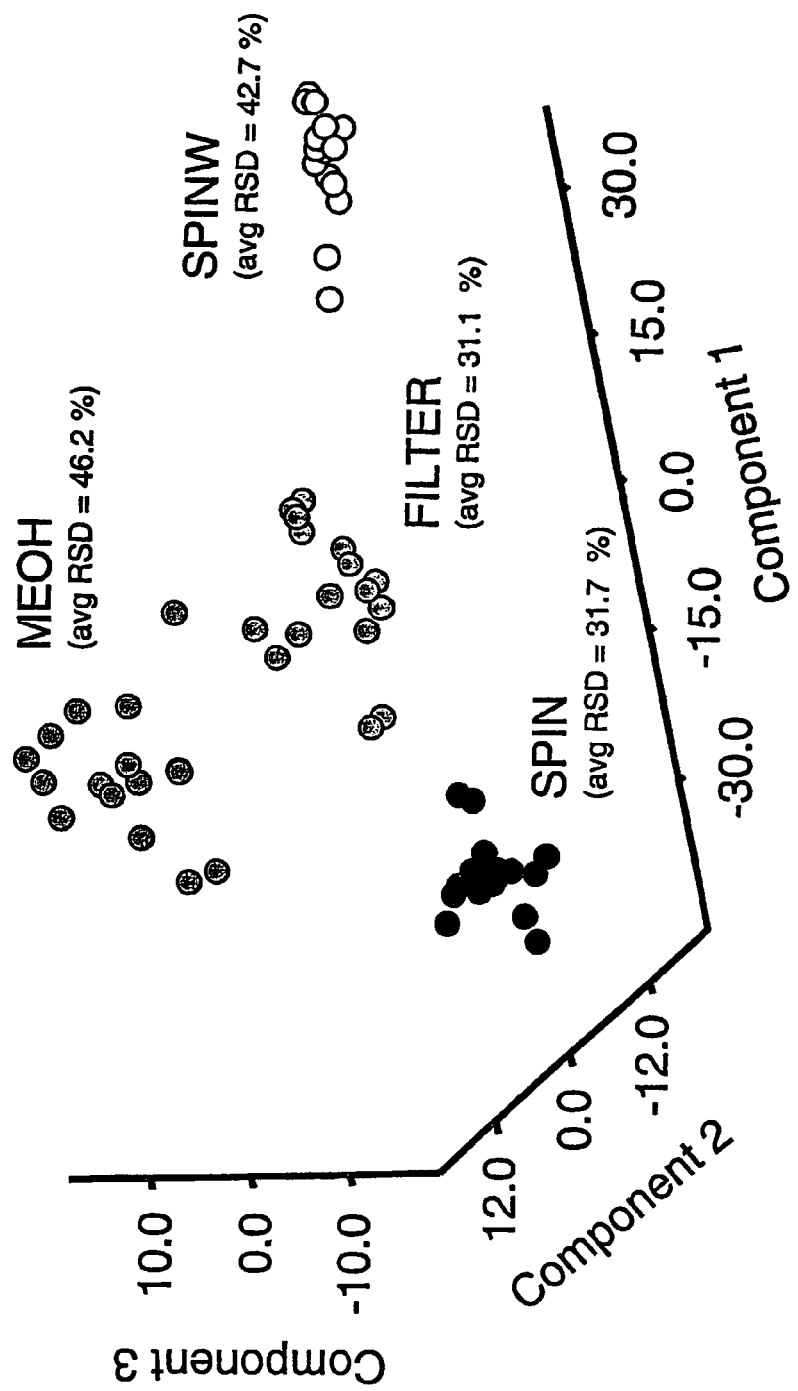

FIG. 5 shows the results of a principal component analyses based on GC-TOF-MS metabolite profiles of extracts from a single batch culture of *Saccharomyces cerevisiae* strain BY4741 ($A_{595} \sim 1.8$). Four sampling strategies (n=16) were employed, namely quenching into cold methanol (MEOH), collection onto filter disc (FILTER), collection by centrifugation without media wash (SPIN), and collection by repeated wash and centrifugation cycles (SPINW). Washes were performed with glucose-free SD medium. Principal components 1, 2, and 3 covered 57.4%, 24.2%, and 6.4% of the total variance of the profile data set. Metabolite responses were normalised to the average metabolite response observed within each sample. Average relative standard deviation (RSD) of each of the sampling procedures is indicated. Underlying metabolite profiles, metabolite responses and relative standard deviations of all metabolites are presented in Table 6.

FIG. 6 provides the results of a comparison of four co-response measures applied to metabolite profiles of *Saccharomyces cerevisiae* strain BY4741 ($A_{595} \sim 1.8$). Kendall's correlation coefficient is compared to Euclidian distance (A), mutual information (B) and Pearson's correlation coefficient (C). Each tuple represents a metabolite/metabolite co-response. Arrows indicate position of exemplary bi-plots presented in double-log 10 scale to the right. Four sampling strategies (n=16) were employed, namely MEOH, FILTER, SPIN, and SPINW. The sampling techniques were as described within the legend to FIG. 5. A complete overview of all pair-wise metabolite/metabolite co-response measures is given in Table 7.

Figure 7:
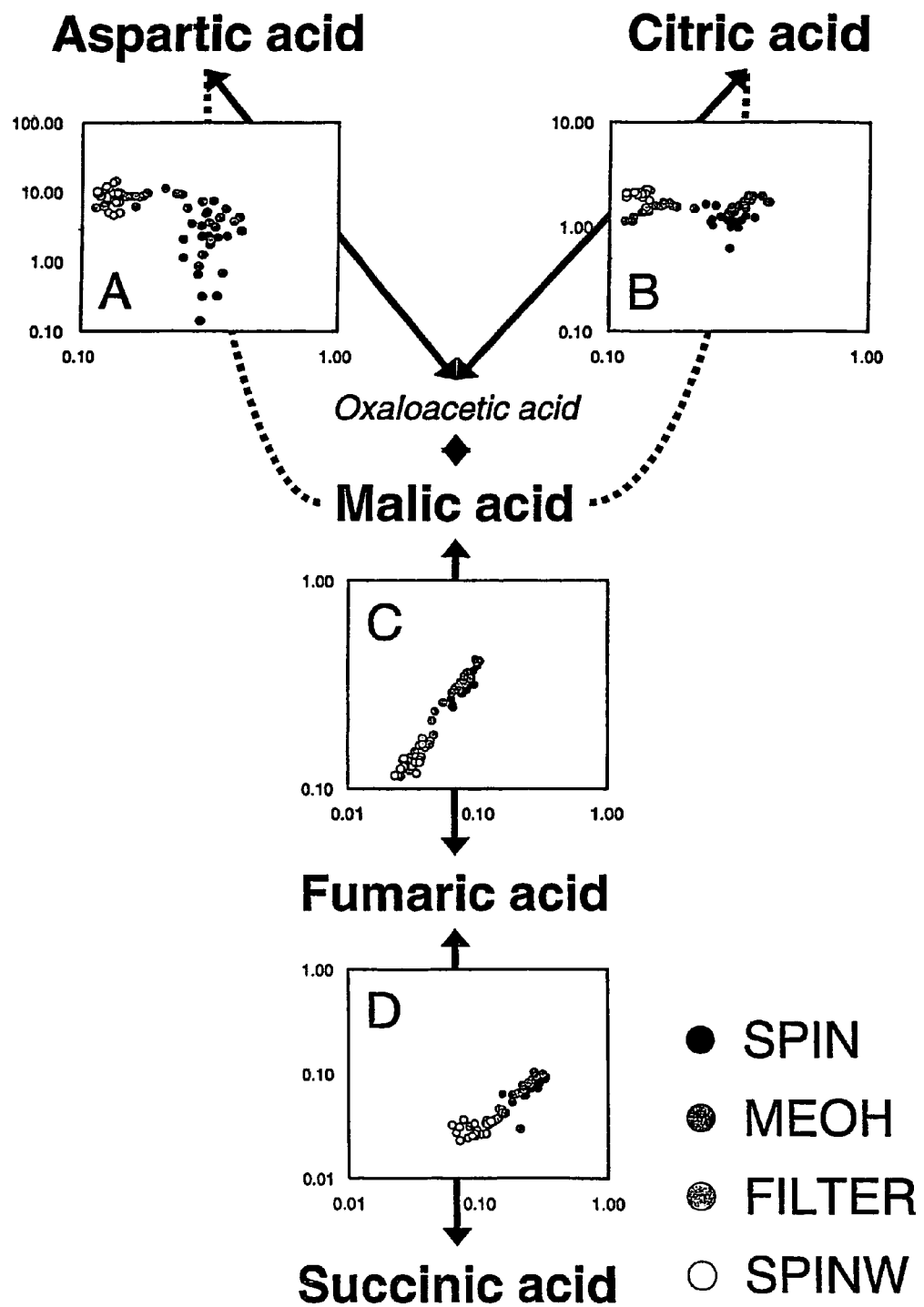
Figure 8:
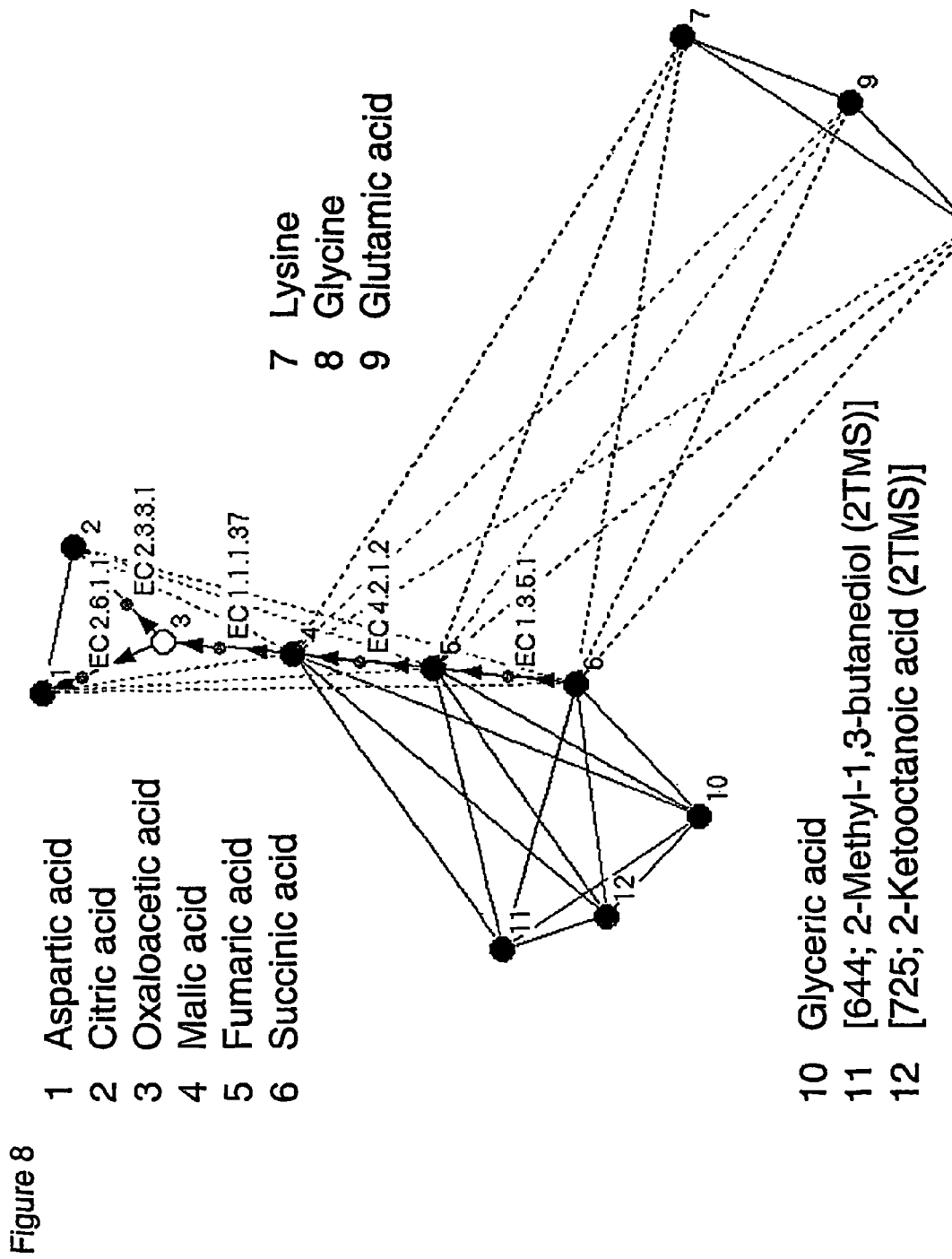

FIG. 7 shows metabolite bi-plots in double-log 10 scale representing co-response behaviour of intermediates and a product of the tricarboxylic acid cycle. Oxaloacetic acid was below limits of detection in GC-TOF-MS profiles of yeast. A, malic acid/aspartic acid; B, malic acid/citric acid; C, fumaric acid/malic acid; D, succinic acid/fumaric acid. The sampling techniques are as described within the legend to FIG. 5.

FIG. 8 shows the common nearest and most distant neighbours of succinic acid, fumaric acid, and malic acid, as described by Kendall's correlation coefficient. Values of correlation coefficients were coded by line style, $\geq 0.6$ full line and $\leq -0.5$ dotted line.

FIG. 9 shows a continuous positive-ion MALDI-TOF-MS spectrum of an ambient $\delta^{13}C$-yeast extract with 2,5-dihydroxybenzoic acid as matrix set to the expected mass range of $NAD^+$ (NADH) adducts, namely protonated molecular ions at m/z 664.11 (666.13), and sodium adducts at m/z 686.09 (688.12), respectively. The inset ($^{12}C/^{13}C$) shows a bar representation of the protonated molecular ion region from a $^{13}C$-isotopomer ratio ($^{13}C$-ITR) MALDI-TOF-MS analyses. M/z 679.26 and 681.25 represent protonated $NAD^+$ and NADH, which were labeled with 15 $^{13}C$-atoms. $^{13}C$-saturated yeast extracts exclusively showed the labeled ions in the m/z 677-685 range (data not shown).

Figure 10:
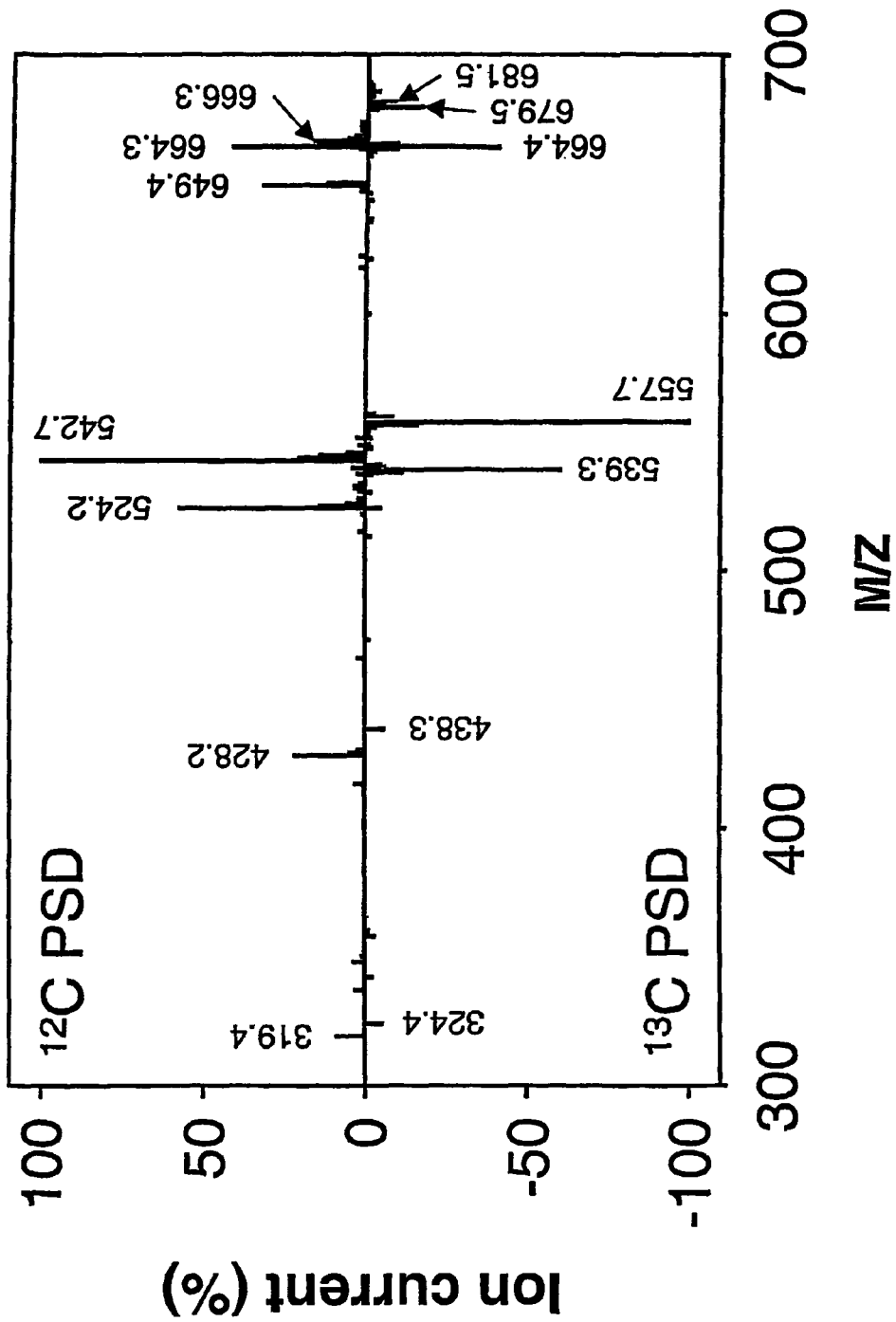

FIG. 10 depicts a head-to-tail analyses of post source decay (PSD) fingerprints from separate MALDI-TOF-MS analyses of ambient $\delta^{13}C$- ($^{12}C$ PSD) and $^{13}C$-saturated ($^{13}C$ PSD) yeast extracts. Evident m/z differences of parent ions and fragments were 15, 10, and 5 amu. The required mass window for the isolation of parent ions ($\sim \pm 3$ amu) and subsequent PSD analyses did not allow separate monitoring of $NAD^+$ and NADH from mixtures.

THE FOLLOWING EXAMPLES ILLUSTRATE THE INVENTION

Experimental Set-Up

Strain Information and In-Vivo Labeling

*Saccharomyces cerevisiae* strains BY4741 (MATa; his3Δ; leu2Δ0; met15Δ0; ura3Δ0) and BY4742 (MATα; his3Δ1; leu2Δ0; lys2Δ0; ura3Δ0) were obtained from the EUROFAN II worldwide gene deletion project (EUROSCARF collection, Frankfurt, Germany. http://www.uni-frankfurt.de/fb15/mikro/euroscarf/col index.html) (Kelly, 2001; Winzeler, 1999). Strains were grown for 16-24 h in 25-250 ml liquid batch cultures on synthetic defined (SD) minimal medium with required auxotrophic supplementation and 20 g $l^{-1}$ ambient $\delta^{13}C$-glucose as major carbon source (Castrillo, 2003). For in-vivo $^{13}C$-labeling ambient glucose was replaced by U-$^{13}C$-glucose (99 atom %, Isotech Inc., Miamisburg, USA). Auxotrophic and vitamin supplements were non-labeled.

For the control of residual SD medium components within cellular preparations from yeast cultures the media contained 4 g $l^{-1}$ lactose (β-D-galactopyranosyl-(1,4)-D-glucose, Fluka, Buchs, Switzerland), which is not utilized by *Saccharomyces cerevisiae*.

Cellular Preparations from Yeast Cultures

For all experiments 5 ml aliquots were taken from overnight yeast batch cultures grown to $A_{595} \sim 1.8$. Sampling procedures were: (1) MEOH, quenching into $-50^\circ$ C. cold methanol, subsequent centrifugation, and aspiration of supematant (MEOH) (Castrillo, 2003; Gonzalez, 1997) with non-buffered quenching solution (see below); (2) FILTER, vacuum collection onto 0.65 μm Durapore PVDF hydrophilic membrane filter discs (Millipore GmbH, Schwalbach, Germany); (3) SPIN, collection by gentle centrifugation and complete aspiration of supernatant without subsequent wash; (4) SPINW, collection by 2 repeated gentle centrifugation and wash cycles with carbohydrate-free SD media. All procedures were performed at $28^\circ$ C. if not mentioned otherwise. Cellular preparations were either immediately processed or shock frozen in liquid nitrogen. Routine sampling was MEOH, if not indicated otherwise. As monitored by the lactose-tracer molecule all sampling methods except SPINW contained low amounts of residual media components. Non-sample control experiments with fresh SD media and analyses of the initial cell free medium and at time of sampling were performed (data not shown).

Preparation of Intracellular Yeast Metabolites

Hot methanol/chloroform extraction (15 min at 70° C.), liquid phase partitioning into methanol/water (1:1, v/v), drying by vacuum centrifugation, and subsequent treatment with methoxyamine hydrochloride (MEOX) and N-methyl-N-(trimethylsilyl)-trifluoroacetamide (MSTFA) reagents for conventional yeast metabolite profiling of polar soluble material was down-scaled as described previously (Wagner, 2003). For the extended GC-TOF-MS analyses of yeast samples liquid partitioning by addition of water to the initial methanol/chloroform extract was omitted. Instead the complete extract volume, ~700 μl, was dried by vacuum centrifugation.

Supplementation of quenching- or extraction-solution with recommended buffer systems (Castrillo, 2003; Gonzalez, 1997) for the preparation of intracellular yeast metabolites led to strong interferences of the buffer substances with either methoxyamination, silylation, or chromatographic performance of the final sample preparations. Therefore, buffering substances had to be avoided for GC-MS profiling.

$^{13}$C-Isotopomer Ratio (ITR) Metabolite Profiling

Extracts of intracellular yeast metabolites from ambient δ$^{13}$C- and $^{13}$C-saturated cultures were combined in equal amounts prior to vacuum centrifugation. The $^{13}$C-saturated extract was treated as a stable isotope labeled, multiplex internal standard mixture. Each component of the resulting metabolite profiles was quantified by use of the respective $^{13}$C-saturated compound. For this purpose $^{12}$C/$^{13}$C response ratios of pre-selected isotopomer fragment pairs were calculated (Table 2). Specific isotopomer fragment pairs were assigned manually to each identified and non-identified metabolite using respective mass spectral entries from the collection of mass spectral metabolite tags (MSTs; see below). Prior to forming ratios responses of $^{13}$C-saturated fragments were corrected for the contribution of naturally occurring $^{13}$C-isotopomers to ambient δ$^{13}$C-preparations.

GC-MS Technologies

Conventional GC-MS profiles were performed with a quadrupole type GC-MS system, namely a GC8000 gas chromatograph coupled to a Voyager mass spectrometer, which was operated by MassLab software (ThermoQuest, Manchester, UK). Modifications to the initial GC-MS profiling method (Fiehn, 2000a; Fiehn, 2000b) were, injection of 1 μl sample in splitless mode, use of a 5° C. min$^{-1}$ temperature ramp with final temperature set to 350° C. on a 30 m×0.25 mm inner diameter Rtx-5Sil MS capillary column with an integrated guard column (Restek GmbH, Bad Homburg, Germany), and use of alkane mixtures for the determination of retention time indices. These changes reflect recent optimisation which was performed with a GC-TOF-Pegasus II MS system (Leco, St. Joseph, USA). All GC-TOF-MS experiments were done on a Pegasus II TOF-MS system as detailed earlier for a diverse range of plant samples (Wagner, 2003)

MALDI-TOF-MS Technologies

Yeast extracts were analysed by MALDI-TOF-MS (Voyager DE-PRO Biospectrometry Workstation, Applied Biosystems, Foster City, USA) set to positive ion detection in reflectron mode (Lerouxel, 2002). Settings for reflectron MALDI-TOF-MS and PSD were as recommended by the manufacturer. A 2,5-dihydroxybenzoic acid (10 mg ml$^{-1}$) matrix was mixed 1:1 (v/v) with polar fractions from yeast extracts or pure compounds, which were dissolved in methanol: water (1:1, v/v). Slow crystallisation by air drying was essential for the laser desorption and ionisation of NAD$^+$ and NADH; microcrystalline samples exhibited complete signal suppression. An exemplary study using the same MALDI-TOF-MS matrix previously demonstrated that stable isotope standardized MALDI-TOF-MS exhibited precise standard curves over two orders of magnitude and produced quantitative results in accordance with in-parallel gas chromatographic analyses (Kang, 2001).

Generation of a Compendium MST Library

MSTs (Table 3) were obtained through automated deconvolution of GC-TOF-MS chromatograms (ChromaTOF™ software, LECO, St. Joseph, USA). Mass spectra were collected into user libraries provided by NIST98 and AMDIS software (http://chemdata.nist.gov/mass-spc/Srch_v1.7index.html and http://chemdata.nist.gov/mass-spc/amdis/; National Institute of Standards and Technology, Gaithersburg, USA) (Stein, 1999; Ausloos, 1999). MSTs were manually annotated and corrected for obvious errors caused by automated deconvolution. Mass spectra of low intensity and truncated or fused mass spectra which resulted from co-elution of compounds were rejected except for demonstrating of the presence of a labeled isotopomer.

Identification and Classification of Mass Spectral Metabolite Tags (MSTs)

MSTs were identified by manually supervised standard addition experiments with pure commercially available substances. Required criteria for substance identification were chromatographic co-elution and high mass spectral similarity of MSTs observed within yeast samples to standard substances (Wagner, 2003) Co-elution and similarity were described by retention time index and mass spectral match values, respectively. Non-identified MSTs were tentatively analysed by best match with a customised MS library of standard substances and entries from the commercial NIST98 library (National Institute of Standards and Technology, Gaithersburg, USA). MSTs were classified by agglomerative hierarchical cluster analyses using Euclidian distance measure and average linkage (Table 5, FIG. 4). Cluster analyses was applied to a complete matrix of pair-wise mass spectral match values (Table 4) as described earlier (Wagner, 2003). Yeast MSTs and a selection of EL-TOF mass spectra from pure standard substances were co-classified.

Statistical Analyses and Visualisation of Metabolite Profiles

Principal component analyses (PCA), hierarchical clustering, calculation of Euclidian distance, Pearson's and Kendall's correlation coefficient, and mutual information was calculated using the S-Plus 2000 software package standard edition release 3 (Insightful, Berlin Germany), the programming language R version 1.6.1 and 1.6.2 (http://www.r-project.org) and the MetaGeneAlyse version 1.3 world wide web resource (http://metagenealyse.mpimp-qolm.mpg.de/) (Daub, 2003).

The model for metabolic network representation was as suggested (Jeong, 2000) and overlay of correlation coefficients in accordance with modularity analyses in metabolic networks (Ravasz, 2002). Network visualisation and layout was performed using the Pajek (Batagelj, 1998) algorithm package available at http://vlado.fmf.uni-lj.si/pub/networks/pajek/.

Calculation of Metabolite Profiles

Each metabolite was represented by a single response value (Table 6). Within GC-MS profiles single metabolites may be represented by multiple derivatives, which are detected by respective MSTs, and each MSTs may be represented by more than one specific fragment (refer to Table 2 and FIG. 1). In these cases an additive composite metabolite response was calculated rather than selecting a single MST and corresponding fragment.

Metabolite response was normalised to the average signal intensity of all MSTs, which were observed within each single GC-MS chromatogram. This strategy of data normalisation was mandatory prior to comparison of sampling technologies and analyses of metabolite co-response, because sampling technologies had variable and different recoveries of viable cells from the same batch culture. For example, each wash cycle of SPINW sampling successively reduced recovery of viable cells (data not shown). Attempts failed to identify a constitutive metabolite, which would allow to exactly monitor the number and size of viable yeast cells within each preparation.

Example 1

Determination of the Extent of Saturation by In Vivo $^{13}$C-Labeling

In order to determine the completeness of in vivo $^{13}$C-labeling (saturation), yeast cells (yeast strain BY 4741; Kelly, 2001; Winzeler, 1999) were fed with U-$^{13}$C-glucose as the only carbon source except for auxotrophic and vitamin supplements, i.e. biotin, pantothenate, folic acid, inositol, niacin, p-aminobenzoic acid, pyridoxine, riboflavin, thiamine, bacto-yeast nitrogen base without amino acids, histidine, leucine, methionine, uracil, and inorganic salts, i.e. ammonium sulfate, boric acid, copper sulfate, potassium iodide, ferric chloride, manganese sulfate, sodium molybdate, zinc sulfate, potassium phosphate, magnesium sulfate, sodium chloride, calcium chloride that were non-labeled and extracts from these yeast cells were examined by conventional electron impact GC-MS for the content of different metabolites. As judged by the resulting mass spectra profiles, the majority of the detectable metabolites from the yeast cells was completely labeled. In detail, ambient (i.e. naturally occurring) $^{12}$C/$^{13}$C-carbon ($\delta^{13}$C-) isotopomer composition was found for uracil, methionine, histidine, nicotinic acid and inositol in extracts prepared from cultures supplemented with U-$^{13}$C glucose. Non-labeled leucine and panthothenic acid were frequently observed, however these metabolites were only abundant at levels close to detection limits. Other vitamins comprised by SD media, e.g. biotin, folic acid, p-aminobenzoic acid, pyridoxine, riboflavin, and thiamine, were below limits of detection or not accessible by GC-MS technology.

Furthermore, homocysteine, and inositol-phosphate were detected devoid of $^{13}$C-label. A still non-identified conjugate of inositol exhibiting high similarity to galactinol was partially labeled, and uridine carried 5 out of 9 possible $^{13}$C atoms. These findings indicate: (1) synthesis of homocysteine from methionine by 5-methyltetrahydropteroyltri-L-glutamate:L-homocysteine S-methyltransferase (EC 2.1.1.14; MET6), (2) a pathway from inositol to inositol-phosphate possibly through phosphatidylinositol synthase (2.7.8.11; PIS) and phospholipase C (3.1.4.11; PLC1) activity, and (3) uracil scavenged by uracil phosphoribosyltransferase (EC 2.4.2.9; FUR1) and subsequent phosphatase action.

Example 2

"Inverse Labeling" of Yeast Cells

L-lysine supplementation of yeast strain BY 4741 was tested in $^{13}$C-saturated cultures. Lysine is the complementary auxotrophic marker substance of the second Saccharomyces cerevisiae strain BY4742 used by the EUROFAN II worldwide gene deletion project (Kelly, 2001; Winzeler, 1999). $^{13}$C-labeling of lysine was suppressed in strain BY4741 when supplemented with this amino acid. Moreover, 2-aminoadipic acid accumulated only in strain BY4742. This results indicates that the bidirectional L-lysine synthesis and degradation pathway which comprises the activities of L-aminoadipate-semialdehyde dehydrogenase (EC 1.2.1.31; LSY2, LYS5), NADP$^+$-, L-glutamate-forming saccharopine dehydrogenase (EC 1.5.1.10; LYS9), and NAD$^+$-, L-lysine-forming saccharopine dehydrogenase (EC 1.5.1.7; LYS1) is interrupted.

Example 3

Identification of $^{12}$C- and $^{13}$C-Isotopomer Pairs

Reliable identification of pairs of $^{12}$C- and $^{13}$C-isotopomers which represent the same metabolite is a prerequisite for accurate isotopomers ratio (ITR) metabolite profiles. Pairs of isotopomers may be identified based on mass spectral fragmentation as well as by chromatographic retention. Initial GC-MS experiments demonstrated that derivatives of commercially available deuterated compounds had significantly smaller retention time indices (RI) than noh-deuterated compounds. For example, 2,3,3,3-D4 alanine (2 TMS), 2,3,3-D3-aspartic acid (3 TMS), 2,3,3,3-D4 alanine (3 TMS), 2,2,3,3-D4-succinic acid (2 TMS), and 2,3,4,4,4,5,5,5-D8-valine (2 TMS) eluted 1.1, 1.8, 2.3, 2.5, and 3.8 RI units prior to respective non-deuterated isotopomers.

In contrast, commercially available $^{13}$C-labeled compounds exhibited only minor shifts in RI. This observation was confirmed by a selection of 66 $^{13}$C-labeled mass spectral metabolite tags (MSTs) observed in standard GC-MS profiles. This testing set of MSTs was selected according to high mass spectral peak purity and presence of at least one abundant and specific fragment which could be employed for selective ion quantification and RI monitoring. The selection comprised derivatives of amino acids, organic acids, sugars, sugar alcohols, sugar phosphates, and a set of 34 non-identified MSTs. The complete list including all available and manually evaluated GC-EI-MS isotopomer fragment pairs is listed in Table 2 (see infra). RI of $^{13}$C-labeled compounds was on average only 0.28 (±0.53 SD) units smaller than those of non-labeled compounds. This slight shift of RI was equivalent to approximately 0.3 sec of retention time.

Interpretation of the EI-MS fragmentation pattern of pairs of ambient $\delta^{13}$C- and $^{13}$C-isotopomers allowed the verification of metabolite identity. Typical EI mass spectra of succinic acid (2 TMS), glycine (3 TMS), and glutamic acid (3TMS), are shown in FIG. 1. The head to tail analyses of ambient $\delta^{13}$C- and $^{13}$C-EI-mass spectra allowed an easy identification of isotopomer fragment pairs for use in ITR metabolic profiling. For example, glutamic acid ($C_5H_9NO_4$) forms a TMS derivative with the sum formula $C_{14}H_{33}NO_4Si_3$ and a relative molecular mass of 363. The molecular ion M$^+$, m/z 363, and the [M-15]$^+$ fragment, m/z 348, which is generated by typical neutral loss of a $CH_3$-radical from a TMS group, correspond to ions being characterized by m/z 368 and m/z 353 in which all 5 carbon atoms of glutamic acid are $^{13}$C-labeled. The fragment [M-117]$^+$, m/z 246, can be matched with the corresponding $^{13}$C-isotopomer fragment, m/z 250. These fragments are formed by neutral loss of a trimethylsilylated carboxyl group, which contains one of the 5 carbon atoms of the glutamic acid. The M$^+$ and [M-15]$^+$ fragments of ambient $\delta^{13}$C- and $^{13}$C-saturated succinic acid (2 TMS), glycine (3 TMS) and glutamic acid (3TMS) are shown in the insets of FIG. 1. These mixed mass spectra were obtained from $^{13}$C-ITR metabolite profiles, i.e. combined analyses of ambient $\delta^{13}$C- and $^{13}$C-saturated yeast extracts within single chromatograms. The chosen examples also demonstrate the necessity to correct $^{13}$C-ITR metabolite profiles for ambient $^{13}$C-isotopomer abundance, especially when the available mass spectral fragments for $^{13}$C-ITR metabolite profiles contain only 1 or 2 labeled carbon atoms.

Example 4

Comparison of $^{13}$C-ITR Metabolite Profiles with Conventionally Produced Metabolite Profiles $^{13}$C-ITR metabolite profiles produced by combining equal amounts of ambient $\delta^{13}$C- and $^{13}$C-saturated yeast extracts into one GC-MS analyses were compared with conventional, i.e. separate, GC-MS profiles of the same extracts. The above-mentioned testing set of yeast MSTs was used for this comparison. Each MST was quantified by up to 3 manually validated isotopomer fragment pairs Table 2 (see infra). This experiment was performed with the aim to establish whether ITR metabolite profiling which utilizes internal standardisation by each the $^{13}$C-labeled compounds is equivalent with conventional metabolite profiling. The latter approach was shown previously to operate successfully by external quantification (Fiehn, 2000a; Roessner, 2000).

Two yeast cultures were grown from the same colony in liquid SD medium. One culture was supplemented with ambient $\delta^{13}$C-glucose, the second with U-$^{13}$C-glucose. Extracts of these cultures were either analysed separately or combined for $^{13}$C-ITR before derivatisation. An initial experiment (Exp1) was repeated by taking a second sample from the same culture after a 15 min time interval (Exp2).

Figure 2D:
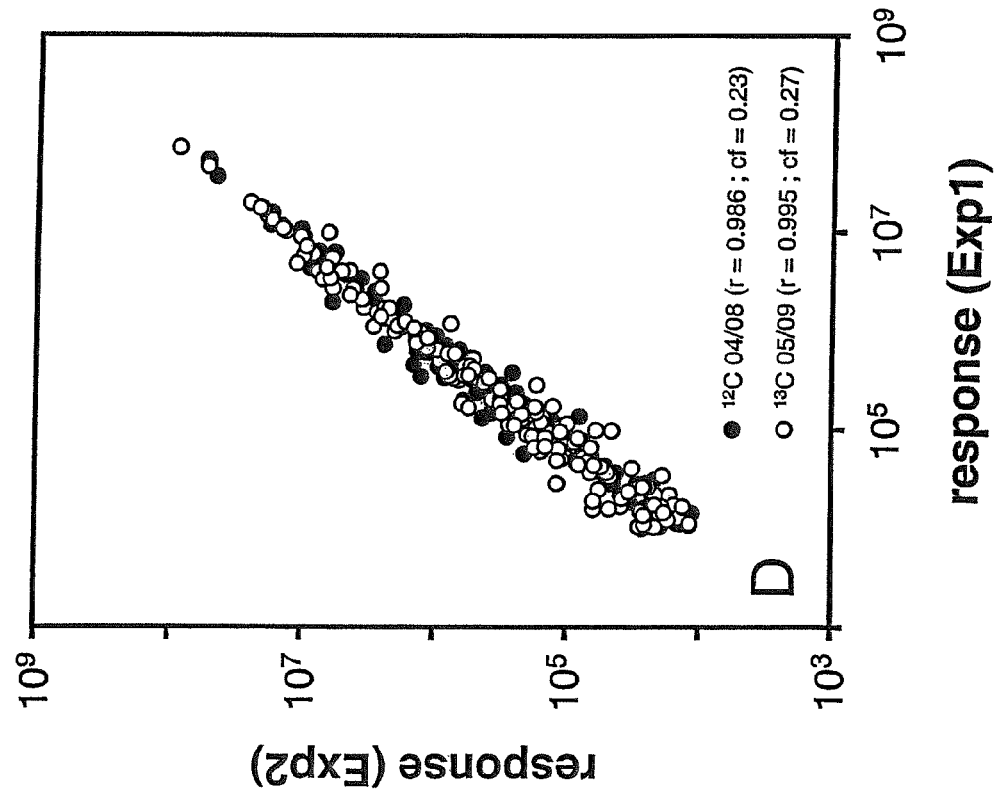
Figure 2C:
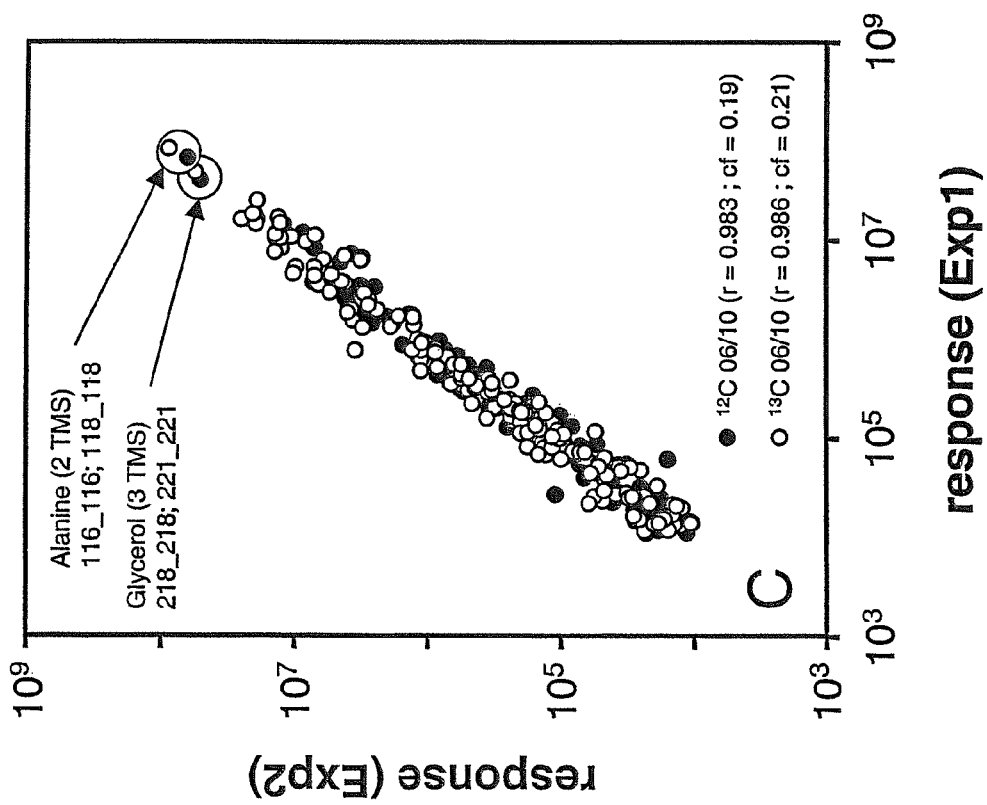

Two comparisons were performed based on the resulting metabolite profiles. (1) Comparison of Exp1 with Exp2 demonstrated the analytical variability, by means of re-analysing the same cultures (FIGS. 2C and 2D). (2) Comparison of the GC-MS responses of the labeled and non-labeled isotopomer fragment pairs showed the effect of $^{13}$C-saturation on metabolic profiles (FIGS. 2A and 2B). Both comparisons were done either by ITR metabolite profiling (FIGS. 2A and 2C; ITR GC-MS analyses 06 and 10) or by conventional metabolite profiling (FIGS. 2B and 2D; ambient $\delta^{13}$C GC-MS analyses 04 and 08; $^{13}$C-saturated GC-MS analyses 05 and 09). GC-MS analyses 04, 05 and 06 represented Exp1, while analyses 08, 09, and 10 comprised Exp2. Pearson's linear correlation coefficient applied to the comparison of the experiments as well as to the influence of $^{13}$C-saturation on the metabolic profiles demonstrated equivalence of ITR metabolite profiling and conventional metabolite profiling (FIG. 2, inset).

The average coefficient of variation was determined by using all fragment pairs which contributed to each of the comparisons. Again results of ITR metabolite profiling and conventional metabolite profiling were equivalent, however, average coefficients of correlation were smaller in ITR metabolite profiling analyses (FIG. 2, inset).

Most of the labeled isotopomers from the $^{13}$C-saturated culture were present in amounts almost equal to the $^{12}$C-isotopomers from the ambient $\delta^{13}$C-culture. The average $^{12}$C/$^{13}$C-isotopomer ratio of all pairs from the complete MST testing set was 0;79 (±0.40 SD). However, some substances exhibited extreme differences, the ratios ranging between 0.01 and 2.98. These observations indicated that the process of $^{13}$C-saturation alone may alter the levels of metabolites. Therefore, ITR metabolite profiling analyses of multiple samples should be standardised by extracts from a single large $^{13}$C-saturated culture and corrected for the systematic error of $^{13}$C-labeling.

Example 5

Preparation of a Compendium of MSTs

Compilations of MSTs from biological samples represent an approach analogous to sequencing projects of expressed sequence tags (EST). We characterised the relevant major metabolites of yeast samples, obtained mass spectra and retention time indices for reliable metabolite identification, and finally generated means for metabolite-specific relative quantification.

Recently introduced GC-TOF-MS technology (van Deursen, 2000; Wagner, 2003) was adapted to the metabolic profiling of yeast. Fast scanning GC-TOF-MS systems are ideally suited for metabolite compendium projects. These systems allow automated and comprehensive deconvolution of mass spectral components from highly complex samples without user intervention. Moreover, this novel technology combines the advantages of high chromatographic resolution and reproducibility with the equally high reproducibility and acquisition rate of non-scanning time-of-flight MS-technology. In vivo stable isotope labeling was used to facilitate one of the most time-consuming steps in establishing metabolite profiling of any given biological sample type, i.e. the task to differentiate between MSTs which originate from yeast metabolism and MSTs which represent experimental contaminations. The stable isotope label was introduced as a chemically defined and predominant carbon source and was used to detect all metabolic conversions originating from this carbon source. The apparent complexity of initial metabolic profiles of polar extracts from yeast was lower than profiles generated for instance from plant sources. We increased the final efficiency of multi-parallel GC-TOF-MS analyses by adapting metabolic profiling to combined chloroform and methanol extracts from yeast which contained lipid metabolites in addition to the metabolites obtained by polar extraction as described earlier. Further attempts to increase the amount of yeast extract to be applied to GC-TOF-MS analyses in order to maximise the number of simultaneously monitored compounds were limited by matrix effects, which were brought about by four predominant compounds, phosphoric acid (3TMS), glycerol (3TMS), glucose (MX, 5TMS), and trehalose (8TMS). The matrix effects resulted (1) from excess phosphoric acid within extracts, which reduced the silylation strength of the MSTFA reagent and (2) from chromatographic overload of derivatives which produced peak deformation artefacts in the vicinity of major peaks. The final amount of yeast extract was adjusted to avoid these matrix effects (FIG. 3). Thus the efficiency of multi-parallel GC-TOF-MS analyses was increased, for the time being without introducing time-consuming pre-fractionation and enrichment protocols.

A compendium of GC-TOF-MS metabolite tags was separately compiled from ambient $\delta^{13}$C- and $^{13}$C-saturated yeast extracts from over-night batch cultures of *Saccharomyces cerevisiae* strain BY4741. In order to obtain different samples the metabolite profiles of which can be compared, different sampling protocols were applied, namely quenching into cold methanol (MEOH), collection onto filter disc (FILTER), collection by centrifugation without media wash (SPIN), and collection by repeated wash and centrifugation cycles (SPINW). The initial set of automatically retrieved mass spectra was manually curated to select MSTs of metabolic origin. The criteria applied for curation were: repeated occurrence of the mass spectral component (n>3), reproducible fragment composition, signal to noise $\geq$50, and presence of a co-eluting $^{13}$C-isotopomer. Mass spectra of metabolite derivatives devoid of carbon, and metabolite derivatives originating from ambient $\delta^{13}C$ auxotrophic and vitamin supplementation were included. The MST compendium is depicted in Table 3.

Example 6

Identification and Classification of MSTs

For the identification of MSTs, mass spectral matching algorithms were employed, which are contained in publicly available mass spectral search and comparison software (Stein, 1999; Ausloos, 1999). The underlying procedures are analogous to those employed in BLAST analyses of ESTs. MSTs were compared to commercial MS collections and a custom EI-TOF-MS library. Best matches were assigned for a preliminary identification (Table 3). However, the presence of multiple chemical isomers with close to identical mass spectral fragmentation patterns make it necessary to conduct standard addition experiments in order to obtain a precise identification. We sampled 180 MSTs (Table 3) and identified 78 tags which represented 67 yeast metabolites (Table 1). The range of identified compounds comprised amino acids, organic acids, sugars, polyols, purines and pyrimidines, phosphorylated compounds, fatty acids and sterols (Table 1).

A non-biased, automated classification of MSTs has previously been established (Wagner, 2003). This approach towards a non-biased mass spectral classification utilises the observation that two mass spectra of the same compound do not only match best but also have similar match values when compared to other, even highly different, mass spectra. This method of MST classification was applied to yeast MSTs and a framework of known mass spectra obtained from standard addition experiments. We inferred 19 groups of MSTs from agglomerative hierarchical clustering by average linkage of Euclidian distances and a cut-off at approximately 50% diversity (FIG. 4 and Table 5). The groups of MSTs comprised alkanes which were included for RI standardisation (group 1; 0/7 non-identified), di- and tri saccharides (group 2; 4/17 non-identified), hexose pyranosides (group 3; 8/9 non-identified), hexonic acids and inositol (group 4; 4/10 non-identified), aldohexose methoxyamines (group 5; 3/12 non-identified), a group of non-identified MSTs similar to polyols (group 6; 5/5 non-identified), ketohexose- and pentose methoxyamines (group 7; 0/14 non-identified), hexitols, pentitols and hexonolactones (group 8; 2/19 non-identified), a group of standard caffeoylquinic acids (group 9; 0/8 non-identified), organic acids and purine nucleosides (group 10; 8/34 non-identified), C3-C5 polyols, hydroxy acids and sugars (group 11; 9/30 non-identified), phosphates (group 12; 9/34 non-identified), amines and amino acids with primary aminogroup (group 14; 8/26 non-identified), fatty acids and sterols (group 15; 7/15 non-identified), a standard set of phenylpropanoic acids (group 16; 0/9 non-identified), a heterogenous group of mostly cyclic compounds comprising phenyl-, indoyl-, imidazol-, pyrimidine-, and purine-residues (group 17; 12/31 non-identified), and a group dominated by amino acids (group 18; 9/60 non-identified). Group 0 (17 MSTS) and group 3 (4 MSTs) represented mass spectra with unclear classification. Most of those mass spectra, which represented identical compounds were found to be either nearest neighbours or were classified to belong to the same branches of the clustering tree. The mass spectrum of leucine (2TMS) was entered in duplicate in order to monitor the position of a pair of identical mass spectra within the clustering tree (FIG. 4). Some yeast MSTs of group 0, namely methionine (2TMS), adenine (2TMS), and proline (2TMS), did not sort as expected. This observation was caused by errors of automated deconvolution due to low abundance or due to co-elution of other MSTs. Clustering after substitution of the matrix by a minimum threshold match value allowed improved grouping of missorted mass spectra, but obscured classification of those MSTs without high similarity to other MSTs or standard MS. More elaborate, preferably supervised-learning algorithms applied to matrices of match values as well as directly to mass spectra and RI will lead to improved and more precise classification results and increased robustness of identification.

Example 7

Application of Metabolite Profiling Analyses

Metabolites are embedded within a network of fast enzyme and transport reactions. Not unexpectedly, metabolite coresponse was discovered within sets of GC-MS metabolite profiles from plant samples. This co-response was subsequently discussed to yield novel information about biochemical mechanisms of metabolite interactions. Because reaction rates of metabolic conversions are in general significantly higher than rates of protein or mRNA turn-over, this type of analyses highly depends on a quick quenching of the metabolizm during sample preparation. However, shock-freezing in liquid nitrogen, which was described earlier to be successful for plant samples, cannot be applied to yeast liquid cultures. For this reason, four other sampling regimes were assessed. These were applied to aliquots from a single batch culture. The sampling strategies were as described above (see Example 5), namely MEOH-, FILTER-, SPIN-, and SPINW-sampling by two repeated wash and centrifugation cycles of SD medium without carbohydrate source. The metabolic perturbation induced by the respective sampling technologies was monitored by GC-TOF-MS metabolite profiles.

Principal component analyses (PCA) of all GC-TOF-MS metabolite profiles demonstrated that each of the sampling strategies exhibited specific metabolic characteristics (FIG. 5). Sampling by repeated wash and centrifugation cycles (SPINW) with glucose-free SD medium was distinct from SPIN sampling and other sampling methods as described by principal component 1, which comprised the bulk variance, 57.4%, of this experiment. Component 2, which held 24.2% of total variance, separated sampling by centrifugation, i.e. SPIN and SPINW, from other sampling technologies. Component 3 comprising 6.4% of total variance still allowed separation of MEOH from FILTER samples. All subsequent principal components were of low descriptive value with respect to the effect of the four sampling technologies. Analyses of the first three component loadings showed that lysine, asparagine, leucine, homoserine, methionine, arabinose, glycerol, octadecanoic acid, and 15 non-identified MSTs contributed most to the variance introduced by the choice of experimental perturbation (Table 6).

All sampling methods tested had a similar range of reproducibility as was indicated by the average relative standard deviation (RSD) of all replicate metabolite measurements (FIG. 5). However, reproducibility of metabolite measurements were in some cases much lower than observed in plant samples. For example, the most widely accepted method, i.e. sampling of yeast cultures into cold methanol (MEOH), exhibited high variation for aspartic and glutamic acid, 67.2% and 91.6% RSD, respectively. This high variance was not caused by a trend over time of sampling or GC-TOF-MS analyses. In contrast, we demonstrated that other sampling strategies allowed highly reproducible measurements of these compounds, as was indicated for example by 18.0% RSD with aspartic acid after FILTER sampling and 7.0% RSD with glutamic acid after SPINW sampling. A complete overview of detailed metabolite-specific data is given in Table 6.

The data provided herein point toward the conclusion that some metabolite pools were in fast transition during or in between MEOH sampling. With respect to some metabolites, for example aspartic acid (FIG. 7A) and glutamic acid, fast SPIN sampling was highly similar to MEOH sampling in exhibiting rapidly changing metabolite pools. Finally, slower sampling technologies, like FILTER and SPINW, apparently allowed adjustment of stable metabolite pools prior to sampling.

Example 8

Metabolite Co-Response Analyses

The analyses presented in Example 7 appear to reflect rapidly changing pool sizes of some metabolites. Thus, the metabolic perturbations, which were caused by the sampling procedures, were employed in order to gain insight into metabolite/metabolite interactions. Four co-response measures, namely Pearson's correlation coefficient, Kendall's correlation coefficient, mutual information (Steuer, 2002), and Euclidian distance, were applied to characterise all pair wise metabolite combinations. The results of these analyses are shown in Table 7.

Pearson's correlation coefficient and Kendall's correlation coefficient were applied to screen for linear co-response, which was reported to prevail in similar analyses of plants. The combination of both parametric and non-parametric tests allowed a preliminary evaluation of the import of outlying measurements on each metabolite co-response. Only a small fraction of apparent linear metabolite co-responses were caused by outlying metabolite measurements (FIG. 6C). When comparing Kendall's and Pearson's correlation coefficients, which were applied to the same metabolite pairs, we observed a roughly sigmoidal relationship with positive and negative linear correlation distributed almost equally. A typical example of a negative linear co-response referring to the metabolite pair glycine/uracil is shown in FIG. 6C.

Mutual information of metabolite pairs plotted over Kendall's correlation coefficient shows a minimum at Kendall's correlation coefficient close to zero. The mutual information measure confirmed positive and negative linear co-response. Moreover, selecting metabolite pairs with high mutual information and low Kendall's correlation coefficient allowed to discriminate non-linear or, as shown for glycine and alanine (FIG. 6B), conditionally linear metabolite co-response.

Euclidian distance proved to be a measure apparently independent of linear correlation (FIG. 6A) or mutual information (data not shown). Euclidian distance, however, was highly efficient in selecting metabolite co-responses which exhibited low variance of both metabolites.

Because each of the correlation measures had different properties, it was refrained in the present work from global hypothesis-free metabolite classification through cluster analyses based on any single distance measure. Instead by selecting intermediates and products of the tricarboxylic acid cycle, we posed the question as to whether the metabolites of a common pathway may be correlated. Succinic acid, fumaric acid, malic acid, aspartic acid, and citric acid were covered by the GC-TOF-MS analyses of yeast cultures presented herein. Aconitic acid, isocitric acid, and 2-oxoglutaric acid can be analysed by GC-TOF-MS profiling but were below limits of detection in this experiment. In a first approach, we focused on those metabolite co-responses which refer to direct links by biochemical reactions (FIG. 7). Highly linear correlations were observed for succinic acid, fumaric acid and malic acid, which were maintained throughout all types of sampling (FIGS. 7C and 7D). By contrast, malic acid and citric acid or aspartic acid, respectively, adopted seemingly independent sampling specific states (FIGS. 7A and 7B). These states were either linear (FIGS. 7A and 7; FILTER subset) or of highly variable and non-linear nature. Other metabolites, which are known to be directly interlinked by biochemical reactions, were also found to be correlated, for example lanosta-8,24-dien-3-beta-ol and ergosterol, glucose-6-phosphate and fructose-6-phosphate, or hexadecanoic acid and octadecanoic acid (Table 7).

In addition, interactions which did not follow classical pathway definitions were found within the data set of metabolite co-responses. For example, we selected a group of corresponding metabolites from a biochemical path of interest, namely succinic acid, fumaric acid, and malic acid, and searched for common closest neighbours. The 3 closest neighbours of this group of organic acids were glyceric acid and two non-identified metabolites as judged by positive Kendall's correlation coefficient. In addition lysine, glycine, and glutamic acid were most distant as judged by negative Kendall's correlation coefficient. An overview of this analyses is shown as a network representation (FIG. 8).

Example 9

$^{13}$C-ITR Metabolite Profiling by MALDI-TOF Mass Spectrometry

Metabolite profiling by GC-TOF-MS was shown to cover about 11% of the 584 yeast metabolites which were predicted by genome-scale reconstruction (Forster, 2003). However, this approach is mainly restricted by the limited scope of the GC-TOF-MS technology. The focus on specific classes of compounds with common properties is inherent to this as well as to any other analytical technology. For this reason, it is demonstrated in connection with the present invention that metabolite profiling using $^{13}$C-in vivo labeling can be extended to MALDI-TOF-MS. MALDI-TOF-MS represents a mass spectral technology, which (1) cannot rely on chromatography for the confirmation of substance identity, (2) is highly sensitive to matrix suppression effects during laser desorption and ionisation, and (3) is not suited for external quantitative calibration. However, using MALDI-TOF for quantification with internal standard substances which are labeled by stable isotopes is an accepted procedure in connection with metabolite flux analyses (Wittmann, 2002; Wittmann, 2001). By nicotinamide adenine dinucleotide (NADH; $C_{21}H_{29}N_7O_{14}P_2$), an ubiquitous metabolic co-factor was chosen which allowed the demonstration of prerequisites essential to the $^{13}$C-ITR approach.

Yeast extracts were treated as described above (see Example 4) to yield samples of a third experiment (Exp3). These samples were each harvested from the same batch cultures. Extracts with ambient $\delta^{13}$C composition, extracts with $^{13}$C-saturated metabolites, and an equal mixture of both extracts were analysed. Screening of MALDI-TOF spectra from the ambient $\delta^{13}$C extract revealed protonated molecular ions of NAD$^+$ and NADH at m/z 664.11 and m/z 666.13, as well as sodium adducts at m/z 686.09 and 688.12 (FIG. 9). These identifications were supported by commercial preparations of NAD$^+$ and NADH. The mass resolution of the MALDI-TOF system did not allow separation of the monoisotopic $^{12}$C-NADH ion from the A+2 isotopomer of ambient NAD$^+$. Therefore, analogous to the quantification of glycine (3TMS) (FIG. 1), correction will be required for the determination of NADH in the presence of NAD$^+$. In addition, MALDI-TOF generated a continuous evenly spaced background of signals (FIG. 9).

Within the mixed sample (FIG. 9, inset), we found isotopomers of the protonated molecular ions of NAD$^+$ and NADH, which contained 15 $^{13}$C-atoms out of 21 carbon atoms present within NAD(H). Small amounts of labeled sodium adducts were present (data not shown). The presence of only 15 labeled carbon atoms was in agreement with the incorporation of non-labeled nicotinamide moieties into NAD(H), which originated from the nicotinic acid vitamin supplement contained in the yeast SD medium. The presence of non-labeled nicotinic acid ($C_6H_5NO_2$) in $^{13}$C-labeled yeast extracts was demonstrated above (Example 1).

The identification of NAD(H) within yeast extracts was confirmed by post source decay (PSD) fingerprints of the protonated molecular ion cluster which were recorded separately from the ambient $\delta^{13}$C and the $^{13}$C-saturated yeast extracts (FIG. 10). Analogous to the comparison of GC-EI-MS fragmentation pattern of isotopomers (FIG. 1), head-to-tail analyses of PSD fingerprints allows the verification of the correct choice of isotopomer pairs. Moreover, fragment analyses of the $^{12}$C-PSD and the $^{13}$C-PSD revealed the successive loss of three moieties containing 5 carbon atoms each, namely two ribose units and one adenine building block, as was indicated by mass differences of 5, 10, and 15, respectively. Due to the restricted resolution of PSD analyses, separate fingerprints of the protonated ions of NAD$^+$ and NADH could not be obtained from mixtures. However, commercially available preparations of NAD$^+$ and NADH indicated that some PSD fragments, for example the fragment m/z 649.4 [M-17]$^+$, were highly specific. Fragment m/z 649.4 may result from facilitated neutral loss of $NH_3$ from the protonated NADH molecular ion. MALDI-TOF preparations of commercially available NAD$^+$ exhibited variable amounts of NADH mainly in the form of ion m/z 666.13, whereas NAD$^+$ was not detectable in preparations from NADH. This last finding indicated that the chosen MALDI-TOF procedure generates a reducing environment for chemical analyses which requires monitoring.

LITERATURE

Aebersold, R. & Mann, M. Mass spectrometry-based proteomics. Nature 422, 198-207 (2003).

Ausloos, P., Clifton, C. L., Lias, S. G., Mikaya, A. I., Stein, S. E., Tchekhovskoi, D. V., Sparkman, O. D., Zaikin, V. & Damo Zhu. The critical evaluation of a comprehensive mass spectral library. J. Am. Soc. Mass Spectrom. 10, 287-299 (1999).

Batagelj, V. & Mrvar, A. Pajek—program for large network analyses. Connections 21, 47-57 (1998).

Birkemeyer, C., Kolasa, A. & Kopka, J. Comprehensive chemical derivatization for gas chromatography-mass spectrometry-based multi-targeted profiling of the major phytohormones. J. Chromatography A 993, 89-102 (2003).

Castrillo, J. I., Hayes, A., Mohammed, S., Gaskell, S. J. & Oliver, S. G. An optimized protocol for metabolome analyses in yeast using direct infusion electrospray mass spectrometry. Phytochemistry 62, 929-937 (2003).

Christensen, B. & Nielsen, J. Isotopomer analyses using GC-MS. Metab. Eng. 1, 282-290 (1999).

Daub, C. O., Kloska, S. & Selbig J. MetaGeneAlyse: Analyses of integrated transcriptional and metabolite data. Bioinformatics (2003 in press).

dos Santos, M. M., Gombert, A. K., Christensen, B., Olsson, L. & Nielsen, J. Identification of in vivo enzyme activities in the cometabolizm of glucose and acetate by Saccharomyces cerevisiae by using $^{13}$C-labeled substrates. Eucaryot. Cell 2, 599-608 (2003).

Duggan, D. J., Bittner, M., Chen, Y. D., Meltzer, P. & Trent, J. M. Expression profiling using cDNA microarrays. Nature Genet. 21(Suppl S), 10-14 (1999).

Fiehn, O., Kopka, J., Dörmann, P., Altmann, T., Trethewey, R. N. & Willmitzer, L. Metabolite profiling for plant functional gemonics. Nat. Biotechnol. 18, 1157-1161 (2000a).

Fiehn, O., Kopka, J., Trethewey, R. N. & Willmitzer, L. Identification of uncommon plant metabolites based on calculation of elemental compositions using gas chromatography and quadrupole mass spectrometry. Anal. Chem. 72, 3573-3580 (2000b).

Forster, J., Famili, I., Fu, P., Palsson, B. O. & Nielsen, J. Genome-scale reconstruction of the Saccharomyces cerevisiae metabolic network. Genome Res. 13, 244-253 (2003).

Gonzalez, B., Francois, J. & Renaud, M. A rapid and reliable method for metabolite extraction in yeast using boiling buffered ethanol. Yeast 13, 1347-1355 (1997).

Goodlett, D. R., & Yi, E. C. Stable isotopic labeling and mass spectrometry as a means to determine differences in protein expression. Trends Anal. Chem. 22, 282-(2003).

Guo, Z., Zhang, Q. C., Zou, H. F., Guo, B. C. & Ni, J. Y. A method for the analyses of low-mass molecules by MALDI-TOF mass spectrometry. Anal. Chem. 74, 1637-1641 (2002).

Gygi, S. P., Rist, B., Gerber, S. A., Turecek, F., Gelb, M. H. & Aebersold, R. Quantitative analyses of complex protein mixtures using isotope-coded affinity tags. Nature Biotech. 17, 994-999 (1999)

Jeong, H., Tombor, B., Albert, R., Oltval, Z. N. & Barabasi, A. L. The large-scale organization of metabolic networks. Nature 407, 651-654 (2000).

Kang, M.-J., Tholey, A. & Heinzle, E. Application of automated matrix-assisted laser desorption/ionisation time-of-flight mass spectrometry for the measurement of enzyme activities. Rapid Commun. Mass Spectrom. 15, 1327-1333 (2001).

Kelly, D. E., Lamb, D. C. & Kelly S. L. Genome-wide generation of yeast gene deletion strains. Comp. Funct. Genomics 2, 236-242 (2001).

Lee, W.-N. P., Byerley, L. O., Bergner, E. A. & Edmond, J. Mass isotopomer analyses: theoretical and practical considerations. Biol. Mass Spectrom. 20, 451-458 (1991).

Lerouxel, O., Choo, T. S., Séveno, M., Usadel, B., Faye, L., Lerouge, P. & Pauly, M. Rapid structural phenotyping of plant cell wall mutants by enzymatic oligosaccharide fingerprinting. Plant Physiol. 130, 1754-1763 (2002).

Lockhart D. J., Dong, H. L., Byrne, M. C., Follettie, M. T., Gallo, M. V., Chee, M. S., Mittmann, M., Wang, C. W., Kobayashi, M., Horton, H. & Brown, E. L. Expression monitoring by hybridization to high-density oligonucleotide arrays. Nature Biotech. 14, 1675-1680 (1996).

Matuszewski, B. K., Constanzer, M. L. & Chavez-Eng, C. M. Strategies for the assessment of matrix effect in quantitative bioanalytical methods based on HPLC-MS/MS. Anal. Chem. 75, 3019-3030 (2003).

Mueller, A., Duechting, P. & Weiler, E. W. A multiplex GC-MS/MS technique for the sensitive and quantitative singlerun analyses of acidic phytohormones and related compounds, and its application to *Arabidopsis thaliana*. Planta 216, 44-56 (2002).

Ravasz, E., Somera, A. L., Mongru, D. A., Oltvai, Z. N. & Barabasi, A.-L. Hierarchical organization of modularity in metabolic networks. Science 297, 1551-1555 (2002).

Roessner, U., Luedemann, A., Brust, D., Fiehn, O., Linke, T., Willmitzer, L. & Fernie, A. R. Metabolic profiling allows comprehensive phenotyping of genetically or environmentally modified plant systems. Plant Cell 13, 11-29 (2001).

Roessner, U., Wagner, C., Kopka, J., Trethewey, R. N. & Willmitzer, L. Simultaneous analyses of metabolites in potato tuber by gas chromatography-mass spectrometry. Plant J. 23, 131-142 (2000).

Schena, M., Shalon, D., Davis, R. W. & Brown, P. O. Quantitative monitoring of gene expression patterns with a complementary DNA microarray. Science 270, 467-470 (1995).

Stein, S. E. An integrated method for spectrum extraction and compound identification from gas chromatography/mass spectrometry data. J. Am. Soc. Mass Spectrom. 10, 770-781 (1999).

Steuer, R., Kurths, J., Daub, C. O., Weise, J. & Selbig, J. The mutual information: Detecting and evaluating dependencies between variables. Bioinformatics 18, S231-S240 Suppl. (2002).

Steuer, R., Kurths, J., Fiehn, O. & Weckwerth, W. Observing and interpreting correlations in metabolomic networks. Bioinformatics 19, 1019-1026 (2003).

Trethewey, R. N., Krotzky, A. J. & Willmitzer, L. Metabolic profiling: A rosetta stone for genomics? Curr. Opin. Plant Biol. 2, 83-85 (1999)

van Deursen, M. M., Beens, J., Janssen, H.-G., Leclercq, P. A. & Cramers, C. A. Evaluation of time-of-flight mass spectrometric detection for fast gas chromatography. J. Chromatogr. A 878, 205-213 (2000).

Wagner, C., Sefkow, M. & Kopka, J. Construction and application of a mass spectral and retention time index database generated from plant GC/EI-TOF-MS metabolite profiles. Phytochemistry 62, 887-900 (2003).

Wiechert, W. $^{13}C$ metabolic flux analysis. Metabolic Engineering 3, 195-206 (2001).

Winzeler, E. A., Shoemaker, D. D., Astromoff, A., Liang, H., Anderson, K., Andre, B., Bangham, R., Benito, R., Boeke, J. D., Bussey, H., Chu, A. M., Connelly, C., Davis, K., Dietrich, F., Dow, S. W., E L Bakkoury, M., Foury, F., Friend, S. H., Gentalen, E., Giaever, G., Hegemann, J. H., Jones, T., Laub, M., Liao, H., Liebundguth, N., Lockhart, D. J., Lucau-Danila, A., Lussier, M., M'Rabet, N., Menard, P., Mittmann, M., Pai, C., Rebischung, C., Revuelta, J. L., Riles, L., Roberts, C. J., Ross-MacDonald, P., Scherens, B., Snyder, M., Sookhai-Mahadeo, S., Storms, R. K., Veronneau, S., Voet, M., Volckaert, G., Ward, T. R., Wysocki, R., Yen, G. S., Yu, K. X., Zimmermann, K., Philippsen, P., Johnston, M. & Davis, R. W. Functional characterization of the *Saccharomyces cerevisiae* genome by gene deletion and parallel analyses. Science 285, 901-906 (1999).

Wittmann, C. & Heinzle E. Application of MALDI-TOF MS to lysine-producing *Corynebacterium glutamicum*. A novel approach for metabolic flux analyses. Eur. J. Biochem. 268, 2441-2455 (2001).

Wittmann, C. Metabolic flux analyses using mass spectrometry. Adv. Biochem. Eng. Biotechnol. 74, 39-64 (2002).

TABLE 1

Table of yeast metabolites, which were represented by at least one mass spectral tag (MST). Identification of MSTs was performed by standard addition experiments. Identification required co-elution, mass spectral similarity, and presence of differentially labeled isotopomers.

Amino acids

2-Aminoadipic acid
Alanine
Arginine
Asparagine
Aspartic acid
Cysteine
Glutamic acid
Glutamine
Glycine
Histidine
Homocysteine
Homoserine
Isoleucine
Leucine
Lysine
Methionine
Ornithine
Phenylalanine
Proline
Pyroglutamic acid
Serine
Threonine
Tryptophan
Tyrosine
Valine Organic acids Citramalic acid
Citric acid
Erythronic acid
Fumaric acid
Gluconic acid
Glyceric acid
Malic acid
Pantothenic acid
Succinic acid Miscellaneous Adenine
Ethanolamine
Nicotinic acid
Uracil
Urea Fatty acids 9-(Z)-Octadecenoic acid
Hexadecanoic acid
Octadecanoic acid
Octadecenoic acid Sterols Ergosterol
Lanosta-8,24-dien-3-beta-ol Sugars alpha-D-Methylglucopyranoside
Arabinose
Ribose
Fructose
Fucose
Glucose
Isomaltose
Mannose
Trehalose Polyols Erythritol
Glycerol
myo-Inositol
Mannitol

TABLE 1-continued

Table of yeast metabolites, which were represented by at least one mass spectral tag (MST). Identification of MSTs was performed by standard addition experiments. Identification required co-elution, mass spectral similarity, and presence of differentially labeled isotopomers.

Ribitol
Sorbitol
Phosphates

Fructose-6-phosphate
Glucose-6-phosphate
Galactose-6-phosphate
Glyceric acid-3-phosphate
Glycerol-2-phosphate
Glycerol-3-phosphate
Phosphoric acid

TABLE 2

The table includes all manually evaluated GC-EI-MS isotopomer fragment pairs of identified and non-identified metabolite derivatives used for $^{13}$C-ITR metabolite profiling. The table comprises names of metabolite derivatives or of best matches, mass spectrum identifier (MS-ID) for cross-referencing with Table 3, mass to charge ratio (M/Z) characterising the fragment isotopomer pairs and deviation of retention time indices ($\Delta$RI).

TABLE 3

Datafile in the format * . . . msp[a] containing all curated GC-EI-TOF-MS mass spectra of MSTs from extracts of *Saccharomyces cerevisiae* strain BY4741.

The spectrum name was designed to allow sorting according to isotopomer, retention time index, experiment, and name, for example 12C__1625.9__1274EC17_Glutamic acid (3TMS) or 12C__1802.0__1313EC75__[706; Xylitol (5TMS)]. Retention time indices are as observed within the indicated experiment. Names represent identifications by co-elution and mass spectral match[b]; names in brackets indicate non-identified compounds and include the best mass spectral match. The chemical ID field was used to group isotopomer mass spectra by a common mass spectral ID (MS-ID), for example 163001-10-1 and 163001-11-1 representing ambient $\delta^{13}$C- and $^{13}$C-saturated isotopomers of glutamic acid (3TMS). This identifier does not represent a CAS registry number. The formatting of this field is predefined by AMDIS software. [a] The file format *.msp can be imported into NIST98 and NIST02 mass spectral comparison software (to be downloaded from http://chemdata.nist.gov/mass-spc/Srch_v1.7/index.html or AMDIS software (to be downloaded from http://chemdata.nist.gov/mass-spc/amdis/). [b] By-products observed in preparations of reference substances were marked (BP).

TABLE 4

Matrix of all mass spectral similarities of the MSTs from yeast which are presented in Table 3. A complete pair-wise matching was performed with NIST98 mass spectral search and comparison software.

TABLE 5

Table of identified and non-identified MSTs from extracts of *Saccharomyces cerevisiae* strain BY4741 and pure standard compounds. MSTs were classified into groups by hierarchical clustering of the complete symmetric matrix of pair-wise mass spectral match values (Table 4). The resulting clustering tree is shown in FIG. 4.

TABLE 6

Table of metabolite responses from GC-TOF-MS metabolite profiles of four sampling strategies (n=6), namely MEOH-, FILTER-, SPIN- and SPINW-sampling by two repeated wash and centrifugation cycles. All samplings were performed on a single batch culture of *Saccharomyces cerevisiae* strain BY4741 ($A_{595}$~1.8). Metabolite responses were normalised by the average metabolite response observed within each sample. MSTs and fragments which comprised the metabolite responses in this set of experiments are indicated. Metabolites exhibiting more than 75% missing data in all types of sampling strategies were removed. Table 6A depicts the raw data values which gave rise to the average values depicted in Table 6B.

TABLE 7

Table of all pair-wise metabolite/metabolite co-response measures. Number of available pair-wise measurements, Euclidian distance, mutual information, Kendall's- and Pearson's correlation coefficient were calculated from the metabolite responses presented in Table 6. The global information content of the correlation measures is demonstrated in FIG. 6.

Lengthy table referenced here

US08420406-20130416-T00001

Please refer to the end of the specification for access instructions.

Lengthy table referenced here

US08420406-20130416-T00002

Please refer to the end of the specification for access instructions.

Lengthy table referenced here

US08420406-20130416-T00003

Please refer to the end of the specification for access instructions.

Lengthy table referenced here

US08420406-20130416-T00004

Please refer to the end of the specification for access instructions.

Lengthy table referenced here

US08420406-20130416-T00005

Please refer to the end of the specification for access instructions.

Lengthy table referenced here

US08420406-20130416-T00006

Please refer to the end of the specification for access instructions.

Lengthy table referenced here

US08420406-20130416-T00007

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08420406B2). An electronic copy of the table will also be available from the USPTO upon request and payment of the fee set forth in 37 CFR 1.19(b)(3).

The invention claimed is:

1. A method for analysing the metabolites of a first biological sample which comprises quantitatively determining at least 50 metabolites in said first sample in a way that said quantitative determination resolves isotopic mass differences within each metabolite, said method comprising
   a) taking a first biological sample from cells which have been maintained under conditions allowing the uptake of an isotopically labeled metabolizable compound in which substantially all atoms of a given element are isotopically labelled so that the metabolites in said cells are saturated with the isotope with which said metabolizable compound is labeled, wherein the proportion of the label-isotope of at least 50 metabolites of the biological sample is increased to at least 80% of the total of all isotopes of the element;
   (b) combining said first biological sample with a second biological sample in which the metabolites are not isotopically labelled or are isotopically labelled differently from the first biological sample;
   (c) separating the metabolites in the samples chromatographically;
   (d) quantitatively determining at least 50 of the metabolites separated in (c) by mass spectrometry;
   (e) obtaining for each quantitatively determined metabolite a matrix of
      (i) chromatographic retention time,
      (ii) mass, and
      (iii) signal strength;
   (f) calculating for each quantitatively determined metabolite of the first and the second sample an isotopomer ratio (ITR) on the basis of the measured signal strengths;
      wherein the at least 50 metabolites comprise sugars, sugar alcohols, organic acids, amino acids, fatty acids, vitamins, sterols, phosphates, polyamines, polyols, nucleosides, adenine, ethanolamine, nicotinic acid, uracil and/or urea.

2. The method of claim 1, wherein the first and the second biological sample correspond to different phenotypic and/or genotypic states of the cells comprised in the samples or from which the samples are derived.

3. The method of claim 2, wherein the different phenotypic and/or genotypic states are different developmental stages, environments, nutritional supplies, taxonomic units, wild-type and mutant or transgenic genomes, infected and uninfected states, diseased and healthy states or different stages of a pathogenicity.

4. The method of claim 1, wherein the isotope is $^{13}C$, $^{15}N$, $^{18}O$ or $^{2}H$.

5. The method of claim 4, wherein the isotopically labeled metabolizable compound is U-$^{13}C$-glucose, $^{2}H_2O$, $H_2^{18}O$, U-$^{13}C$ acidic acid, $^{13}C$ carbonate or $^{13}C$ carbonic acid.

6. The method of claim 1, wherein the biological sample comprises yeast cells or plant cells.

7. The method of claim 1, wherein mass spectrometry is MALDI-TOF.

8. The method of claim 1, further comprising the step of introducing external standards for one or more of the quantitatively determined metabolites.

9. The method of claim 1, further comprising the step of identifying the metabolites which are quantitatively determined.

10. The method of claim 9, wherein said metabolites are identified by secondary fragmentation.

11. The method of claim 10, wherein identifying of said metabolites comprises electron impact ionisation, MS-MS technology and/or post source decay analyses of molecular ions or fragments.

12. The method of claim 1, wherein, in addition to metabolites, one or more proteins and/or RNA transcripts in said sample are quantitatively determined and analysed.

13. The method of claim 1, wherein said analysing further involves suitable statistical evaluation and correlation analyses of the data obtained and, optionally, network analyses.

14. A kit comprising an isotopically labeled metabolizable compound and a manual for use in carrying in out the method of claim 1.

* * * * *